US009050121B2

(12) United States Patent
Doyle

(10) Patent No.: US 9,050,121 B2
(45) Date of Patent: Jun. 9, 2015

(54) HYDRAULIC DEVICE INCLUDING A SPOOL VALVE AND METHOD OF USE THEREOF

(75) Inventor: Mark Doyle, Del Mar, CA (US)

(73) Assignee: CAREFUSION 2200, INC., San Diego, CA (US)

( * ) Notice: Subject to any disclaimer, the term of this patent is extended or adjusted under 35 U.S.C. 154(b) by 395 days.

(21) Appl. No.: 13/521,195

(22) PCT Filed: Jan. 21, 2011

(86) PCT No.: PCT/US2011/022086
§ 371 (c)(1),
(2), (4) Date: Dec. 26, 2012

(87) PCT Pub. No.: WO2011/091273
PCT Pub. Date: Jul. 28, 2011

(65) Prior Publication Data
US 2013/0090668 A1    Apr. 11, 2013

Related U.S. Application Data

(60) Provisional application No. 61/297,630, filed on Jan. 22, 2010.

(51) Int. Cl.
*A61B 19/00* (2006.01)
*F15B 13/04* (2006.01)
*F16K 11/07* (2006.01)
*F16K 3/26* (2006.01)

(52) U.S. Cl.
CPC ......... *A61B 19/2203* (2013.01); *F15B 13/0402* (2013.01); *F16K 11/0716* (2013.01); *F16K 3/26* (2013.01)

(58) Field of Classification Search
CPC ...................................................... A61B 19/00
USPC ............... 60/571, 572, 591, 584; 137/625.49
See application file for complete search history.

(56) References Cited

U.S. PATENT DOCUMENTS

| 2,969,045 | A | * | 1/1961 | Clar .......................... 137/625.65 |
| 2,988,306 | A | * | 6/1961 | Kutzler ......................... 244/78.1 |
| 3,526,247 | A | * | 9/1970 | McMillen ................. 137/596.13 |
| 3,827,453 | A | * | 8/1974 | Malott et al. .............. 137/115.21 |
| 4,951,861 | A | | 8/1990 | Schulze et al. |
| 5,361,583 | A | | 11/1994 | Huitema |
| 6,722,385 | B1 | | 4/2004 | Bolaski |
| 6,782,796 | B2 | * | 8/2004 | Nakano ........................... 91/434 |
| 6,796,339 | B1 | * | 9/2004 | Petty ............................... 141/65 |
| 7,169,141 | B2 | * | 1/2007 | Brock et al. ....................... 606/1 |
| 7,470,268 | B2 | | 12/2008 | Doyle et al. |
| 8,069,661 | B2 | * | 12/2011 | Hendrickson et al. .......... 60/417 |

(Continued)

*Primary Examiner* — Craig Schneider
*Assistant Examiner* — Christopher Ballman
(74) *Attorney, Agent, or Firm* — Arent Fox LLP

(57) ABSTRACT

A spool valve for controlling fluid communication among hydraulic cylinders operating control and slave portions of a surgical device. The spool valve may be used to disconnect the control and the slave portions from one another such that there is no fluid communication between the control and slave portions. The spool valve may be used to engage or allow fluid communication between the control and slave. The spool valve may also be used to allow fluid communication between the slave and control portion and a fluid reservoir, thus allowing the hydraulic system to replenish fluid lost to evaporation, leakage, or other escape. The spool valve includes a body portion having at least two ports and a spool having at least one passageway moveable to a position so as to communicate with the at least two ports.

29 Claims, 19 Drawing Sheets

(56) References Cited

U.S. PATENT DOCUMENTS

| | | | |
|---|---|---|---|
| 8,292,051 B2 * | 10/2012 | Cadeddu et al. | 188/345 |
| 2003/0013949 A1 * | 1/2003 | Moll et al. | 600/407 |
| 2008/0103437 A1 * | 5/2008 | Duchon et al. | 604/67 |
| 2010/0012195 A1 * | 1/2010 | Hunnicutt | 137/1 |
| 2014/0157771 A1 * | 6/2014 | Jeon et al. | 60/591 |

* cited by examiner

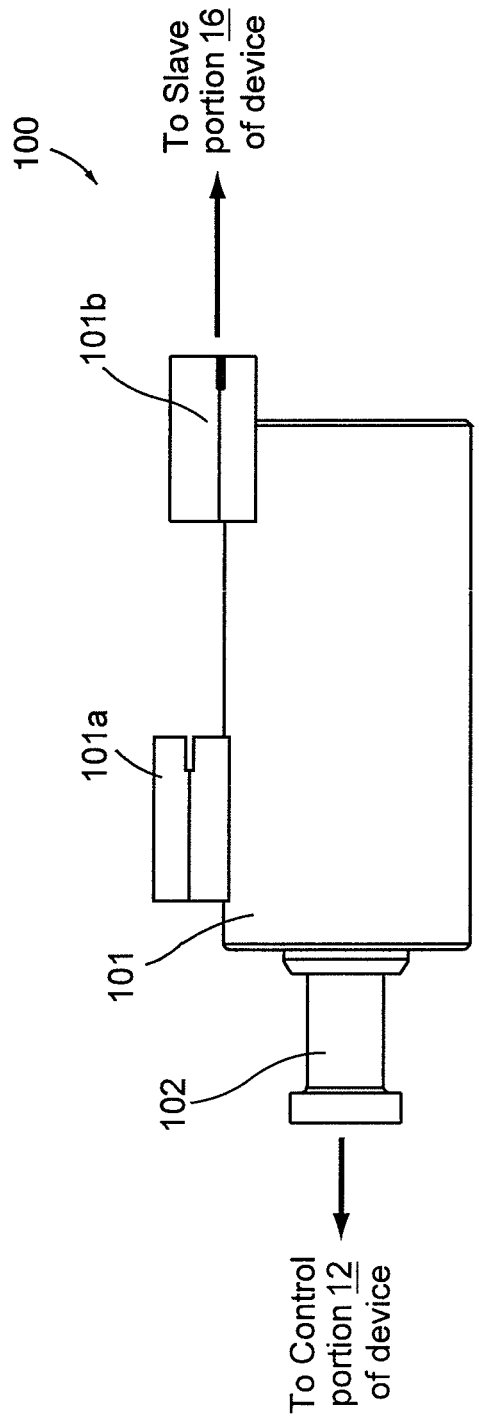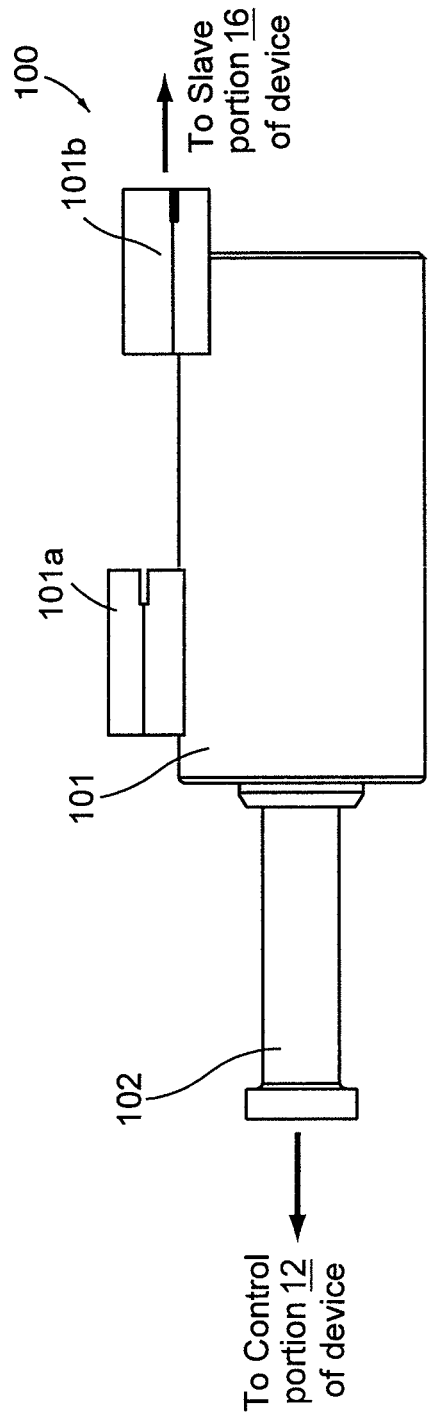
Figure 3A
Figure 3B

HYDRAULIC DEVICE INCLUDING A SPOOL VALVE AND METHOD OF USE THEREOF

This application claims priority to U.S. Provisional Application No. 61/297,630, which was filed on Jan. 22, 2010, the entirety of which is hereby incorporated by reference herein. This application is also related to Applicant's co-pending International Application No. PCT/US10/46619 titled "ARTICULATED SURGICAL TOOL" filed on Aug. 25, 2010, the entirety of which is hereby incorporated by reference herein.

BACKGROUND

1. Field of the Invention

Aspects of the present invention relate to a hydraulic device, and more particularly to a hydraulic device including a spool valve.

2. Background of the Related Art

Related art hydraulic systems for applications in laparoscopic surgical tools, as well as tools for other surgical procedures, are known. However, current laparoscopic surgical instruments typically have considerable limitations, including those relating to their capability to access portions of the body obstructed by organs or other obstructions, and related art devices are typically difficult to sterilize. Furthermore, these devices often utilize straight bodies and/or other tools that that are awkward and difficult to use.

Moreover, related art laparoscopic surgical instruments typically use cables and hydraulic lines to manipulate the surgical tip of the instruments. The hydraulics often require the use of special hydraulic fluid that is not necessarily amenable to surgical environments or other special environments. For example, the use of conventional hydraulic oils in surgical environments is ill-advised and may create an assortment of hazards, especially if the system leaks or the hydraulic conduits are prone to rupture. While more medically compatible hydraulic fluid may be used (e.g., water, mineral oils), such fluid tends to evaporate at a significant rate. Monitoring and replenishing such fluid manually can be costly and labor intensive. Further, the consequences of not being vigilant concerning fluid levels could be severe, particularly in a surgical environment.

Moreover, related art laparoscopic surgical instruments using cables and hydraulic lines to remotely manipulate the surgical tip of the instruments can be vulnerable to accidental misuse or user overcompensation sometimes due to a lack of direct tactile feedback. This danger is particularly significant when the apparatus is not in deliberate use (e.g., dormant during a critical portion of surgery where other equipment is being used), is being serviced/stored or is not being operated by a skilled practitioner. Inadvertent and potentially damaging maneuvers are possible, for example, when the device is moved between operating theaters or when routine maintenance is being performed. In particular, problems can arise when a user moves a control for a laparoscopic surgical device in such a way that can cause damage either to the device itself, to ancillary devices and/or to the patient.

Thus, there is a need in the art for improved hydraulic devices, and more particularly, for improved hydraulic surgical systems.

SUMMARY

While discussion of the aspects of the present invention that follows uses surgery for an illustrative purpose, it should be appreciated that the environment thereof is not limited to surgery and may be used in a variety of other environments. In particular, variations of the invention described herein can be used in any suitable hydraulic device or application. For example, aspects of the present invention may be used in manufacturing, construction, assembly lines, handling and disposing of hazardous materials, underwater manipulations, handling high temperature materials, or any other suitable environment where a user may be remote from the item being manipulated or may experience fatigue when operating a mechanical device.

In one aspect of the present invention, a single spool valve controls fluid communication between hydraulic cylinders operating in the control and slave portions of the device. In particular, the single spool valve may be used to disconnect the control and the slave portions of a hydraulic device from one another, such that there is little or no fluid communication between the control and slave portions of the device. This mode, called "brake mode," prevents inadvertent motion during surgical procedure or other use. Further, such a mode can also serve to immobilize certain portions of the device during operations that require those portions to be immobilized. The single spool valve may be used to engage or allow fluid communication between the control and slave portions of the device. This mode, called "use mode," may enable the user to operate the device to the full extent of its mechanical capability. The single spool valve may also be used to allow fluid communication between the slave and control portion of the device and a fluid reservoir, thus allowing the hydraulic system to replenish fluid lost to evaporation or leakage, for example. This mode, called "storage mode," can allow the device to be stored, moved or serviced over extended or short periods without a substantial loss in hydraulic fluid.

In accordance with another aspect of the present invention, multiple spool valves may be used for multiple components on the same device. The spool valves may, for example, be used on different mechanical controls or on controls for different aspects of the same mechanical operations. The multiple spool valves may be identical or very similar, or they may vary substantially, depending on the particular application. Moreover, a spool valve according to aspects of this invention may omit or not include each of the aspects discussed herein (e.g., a spool valve according to aspects of this invention may not have a brake mode).

In another aspect of the present invention, spool valves may be used that incorporate O-rings to seal one or more of the connections between the spool valve and hydraulic lines. In yet another aspect of the present invention, spool valves may be used that incorporate seal tubes to seal connections between the spool valve and one or more hydraulic lines. In still another aspect of the present invention, spool valves may be used that incorporate both O-rings and seal tubes to seal one or more the connections between the spool valve and the hydraulic lines.

Aspects of the present invention may provide benefits and advantages that include the ability to prevent unwanted motion and resulting damage to hydraulically actuated systems. Aspects of the present invention may also provide benefits and advantages that include replenishing of hydraulic fluid. Thus, hydraulic systems can be made more robust and precision hydraulic instrumentation can be used in environments that would otherwise compromise relatively delicate equipment.

Additional advantages and novel features relating to aspects of the present invention will be set forth in part in the description that follows, and in part will become more apparent to those skilled in the art upon examination of the following or upon learning by practice of aspects thereof.

BRIEF DESCRIPTION OF THE DRAWINGS

Aspects of the present invention will become fully understood from the detailed description given herein below and the accompanying drawings, which are given by way of illustration and example only and thus are not limited with respect to aspects of the present invention, wherein:

FIG. 3A is a side view of an exemplary control cylinder in the retracted position in accordance with aspects of the present invention;

FIG. 3B is a side view of an exemplary control cylinder in the extended position in accordance with aspects of the present invention;

DETAILED DESCRIPTION

Aspects of the present invention will now be described more fully hereinafter with reference to the accompanying drawings, in which variations and exemplary features of the present invention are shown. Aspects of the present invention may, however, be realized in many different forms and should not be construed as limited to the variations set forth herein; rather, the variations are provided so that this disclosure will be thorough and complete in the illustrative implementations, and will fully convey the scope thereof to those skilled in the art.

Unless otherwise defined, all technical and scientific terms used herein have the same meaning as commonly understood by one of ordinary skill in the art to which aspects of the present invention belong. The methods and examples provided herein are illustrative only and not intended to be limiting.

Figure 1:
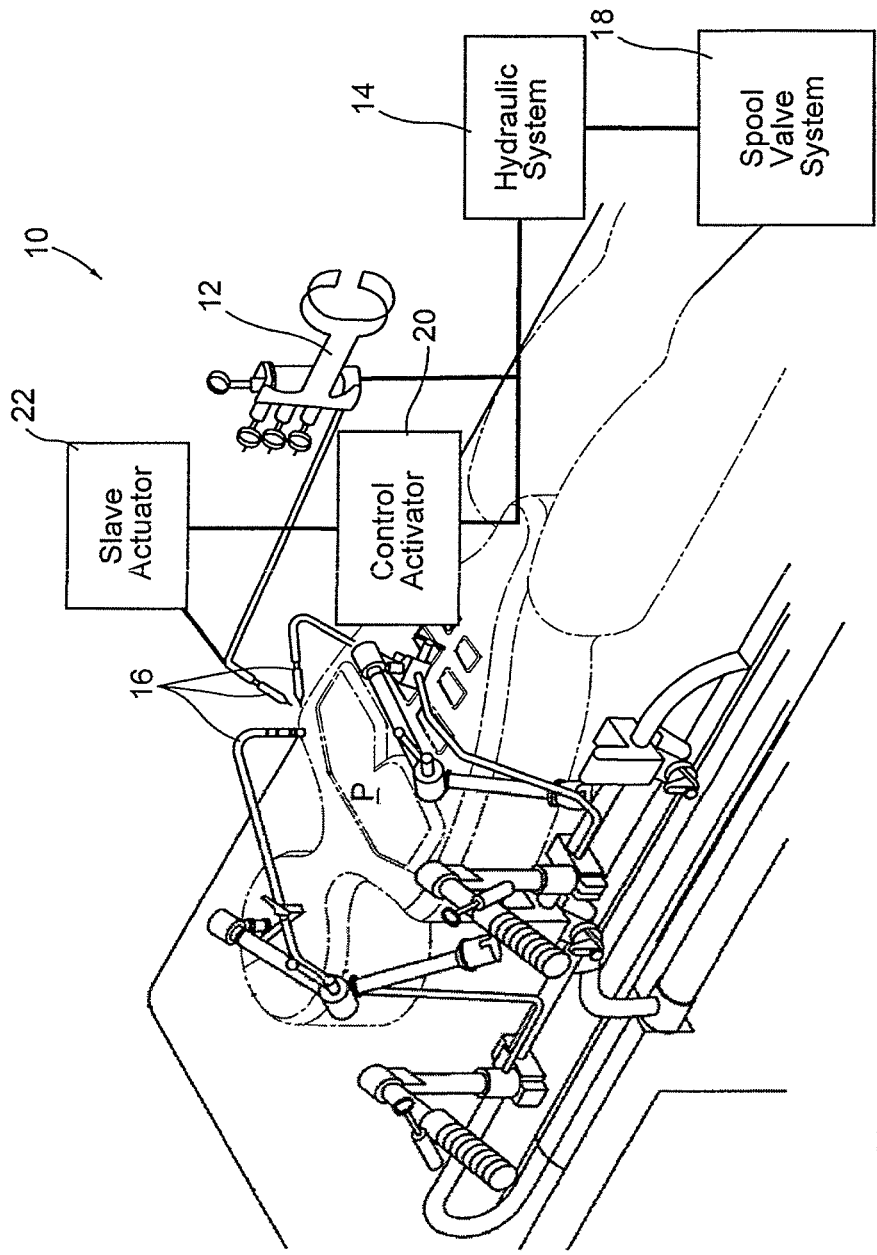
FIG. 1 is a perspective view of an exemplary system in which aspects of the present invention could be utilized in performing surgery on a patent.

FIG. 1 is a schematic diagram of an exemplary device 10, such as a surgical system, that receives a user input at one or more control portion(s) 12 and transfers those inputs via a hydraulic system 14 to one or more slave portion(s) 16 for performing work. Hydraulic system 14 includes a spool valve system 18, which may be configured for one or any combination of: enhancing the control and manipulation of the device; permitting different states of fluid communication between various actuating cylinders in the device; and, retaining and replenishing hydraulic fluid in hydraulic system 14 or device 10. In one variation, which should not be construed as limiting, aspects of the present invention could be utilized in performing surgery on a patent P. For example, the device 10 may include a surgical system as described in more detail in U.S. Pat. No. 6,607,475, which is hereby incorporated by reference herein. For instance, the device 10 may include any number of suitable driven mechanical devices to assist in the performance of surgery, maintenance or other operations. Although FIG. 1 shows a surgical device 10, it is to be understood that aspects of the present invention can be used in conjunction with any suitable device with mechanical actuating features. Some of the driven mechanical devices, such as the one shown in FIG. 1, may include one or more control actuators 20 hydraulically connected to a corresponding one or more slave actuators 22 in order to transfer a received user input to a working end of slave portion 16 of device 10. Each of the control actuator 20 and the slave actuator 22 may include a hydraulic cylinder, which includes a cylinder, a piston, a shaft and other features common to hydraulic cylinders. In one variation, for example, the control actuator 20 receives an input, such as a movement of a part of control portion 12 by a surgeon, and transfers that input, directly or in some predetermined proportion, to the slave actuator 22 to actuate a mechanical operation in an end effector or tool connected to the slave portion 16 of the device 10. Generally speaking, the input mechanism(s) and one or more control actuators 20 may be part of the control portion 12 of the device 10, and the one or more slave actuators 22 and/or one or more end effectors or tools may be part of the slave portion 16 of the device 10. The connections between the control portion 12 and slave portion 16 may be primarily hydraulic in nature to allow transmission of mechanical forces between the two portions. It should be noted, however, that other connections (e.g., electrical, pneumatic, electromagnetic, optical, and/or other mechanical elements) may also be present in order to transmit various types of information between the two portions of the device.

Figure 2A:
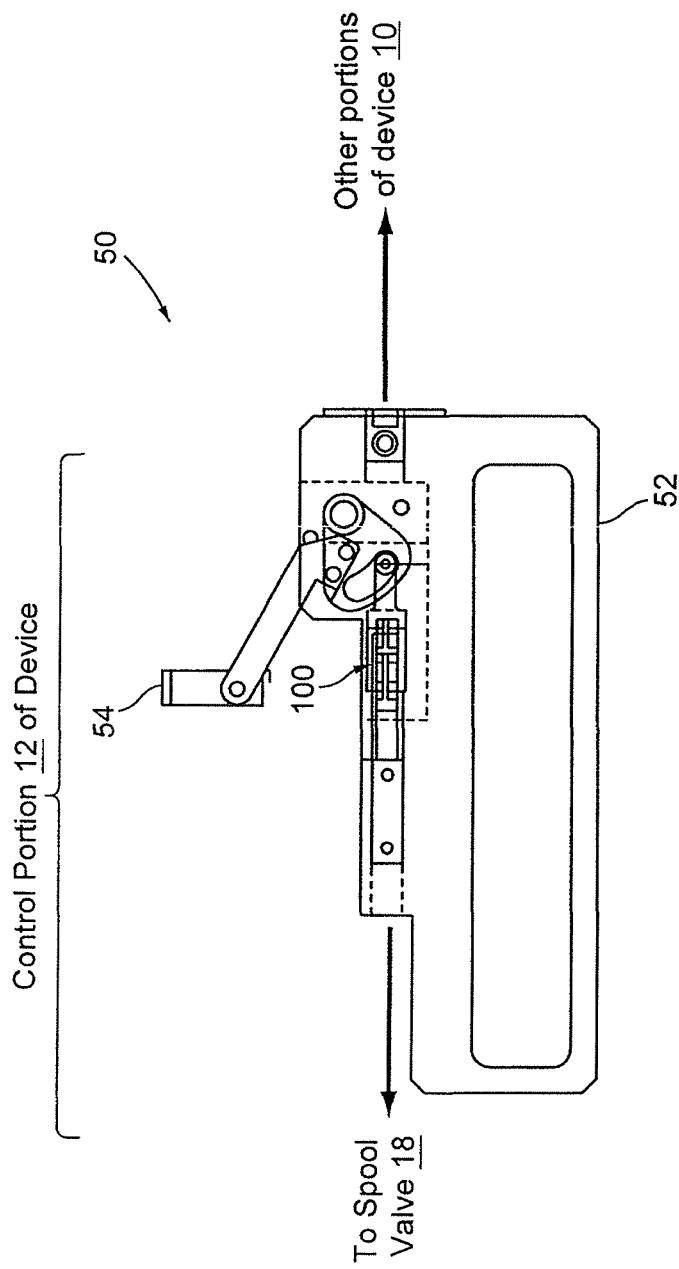
FIG. 2A is a side view of one variation of an exemplary control unit that may be used in conjunction with aspects of the present invention.

FIG. 2A is a detailed drawing of one variation of an exemplary control unit 50 that may be used in conjunction with the control portion 12 (FIG. 1), in accordance with aspects of the present invention. FIG. 2A shows several exemplary features of the control unit 50, including a handle 52, and a thumb loop 54 for interacting with the user. Generally, the user may grasp the handle 52, place a thumb inside the thumb loop 54, and squeeze. This and similar motions generally effect a mechanical response in a control cylinder 100, which transmits the mechanical response to another portion of the device, such as the slave portion 16. Also, control cylinder 100 may be connected to spool valve system 18. As will be described in detail below, one purpose of the spool valve system 18 in variations of the instant invention, among others, is to control fluid communication between the control cylinder 100 and the slave portion 16 of the device 10. Note that the control unit 50 in FIG. 2A is an example of one of any number or types of control units that may be used in conjunction with the control portion 12 (FIG. 1).

Figure 2B:
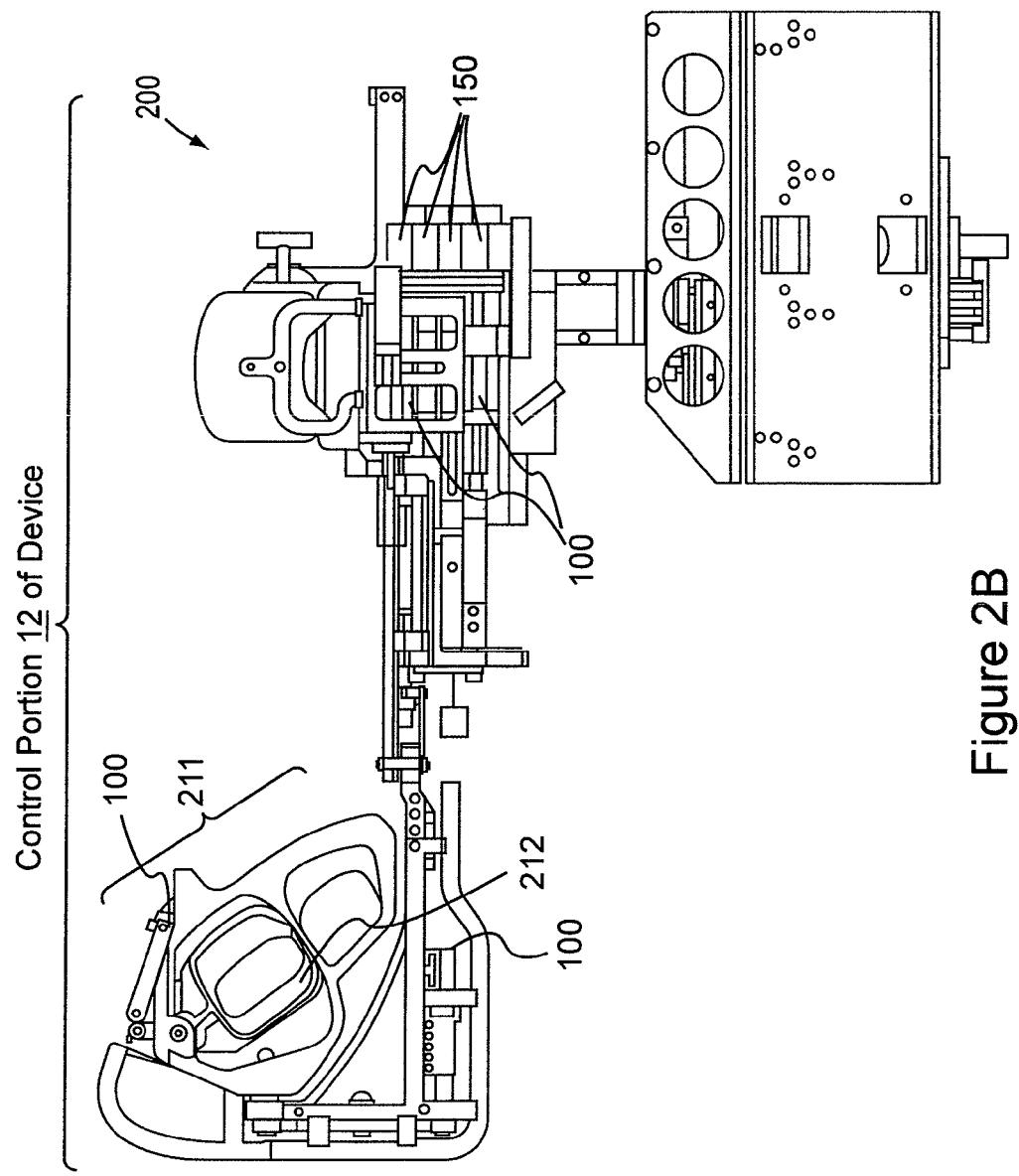
FIG. 2B is a side view of another variation of an exemplary control unit that may be used in conjunction with aspects of the present invention.

FIG. 2B is a detailed drawing of another variation of an exemplary control unit 200 that may be used in conjunction with the control portion 12 (FIG. 1). FIG. 2B shows several exemplary features of the control unit 200, including a handle 211, and a trigger loop 212 for interacting with the user. The control unit 200 differs from the exemplary control unit 50 of FIG. 2A in that control unit 200 allows more degrees of freedom in the motions that may be transmitted from the control portion 12 to the slave portion 16 of the device 10. In some aspects, each degree of freedom corresponds to a corresponding control cylinder 100, and thus control unit 200 may include a plurality of control cylinders. Generally, to operate control unit 200, the user may grasp the handle 211, place one or more fingers inside the trigger loop 212 and squeeze the trigger loop 212, as well as move the handle 211 in various directions. This motion and similar motions generally produce a mechanical response in one or more respective control cylinders 100, which transmit the mechanical response to the corresponding one or more slave actuators 22 in the slave portion 16 of the device 10.

Additionally, control unit 200 may include one or more spool valves 150 connected to a respective one or more of the control cylinders 100. The spool valves 150 are generally connected to each of the control cylinders 100 at one end, or on one side of the respective piston, and contain a portion of the control fluid communicating between the control cylinder 100 and the slave portion 16 of the device 10. For example, each spool valve 150 may fluidly communicate via a port with the control cylinder 100, and fluidly communicate via an outlet with the slave actuator 16, as will be described in more detail below. For example, the connection may include a respective hydraulic line communicating between each of the control actuators 20 a corresponding slave actuator 22. In this configuration, each degree of freedom controlled by control unit 200 may have one control cylinder (control actuator 20) in the control portion 12 and one control cylinder (slave actuator 22) in the slave portion 16 associated with it, with the spool valves 150 also forming part of the fluid path or connection. Note that the control unit 200 in FIG. 2B is purely exemplary of one of the types of control units that may be used in the control portion 12, in accordance with aspects of the present invention.

Figure 2C:
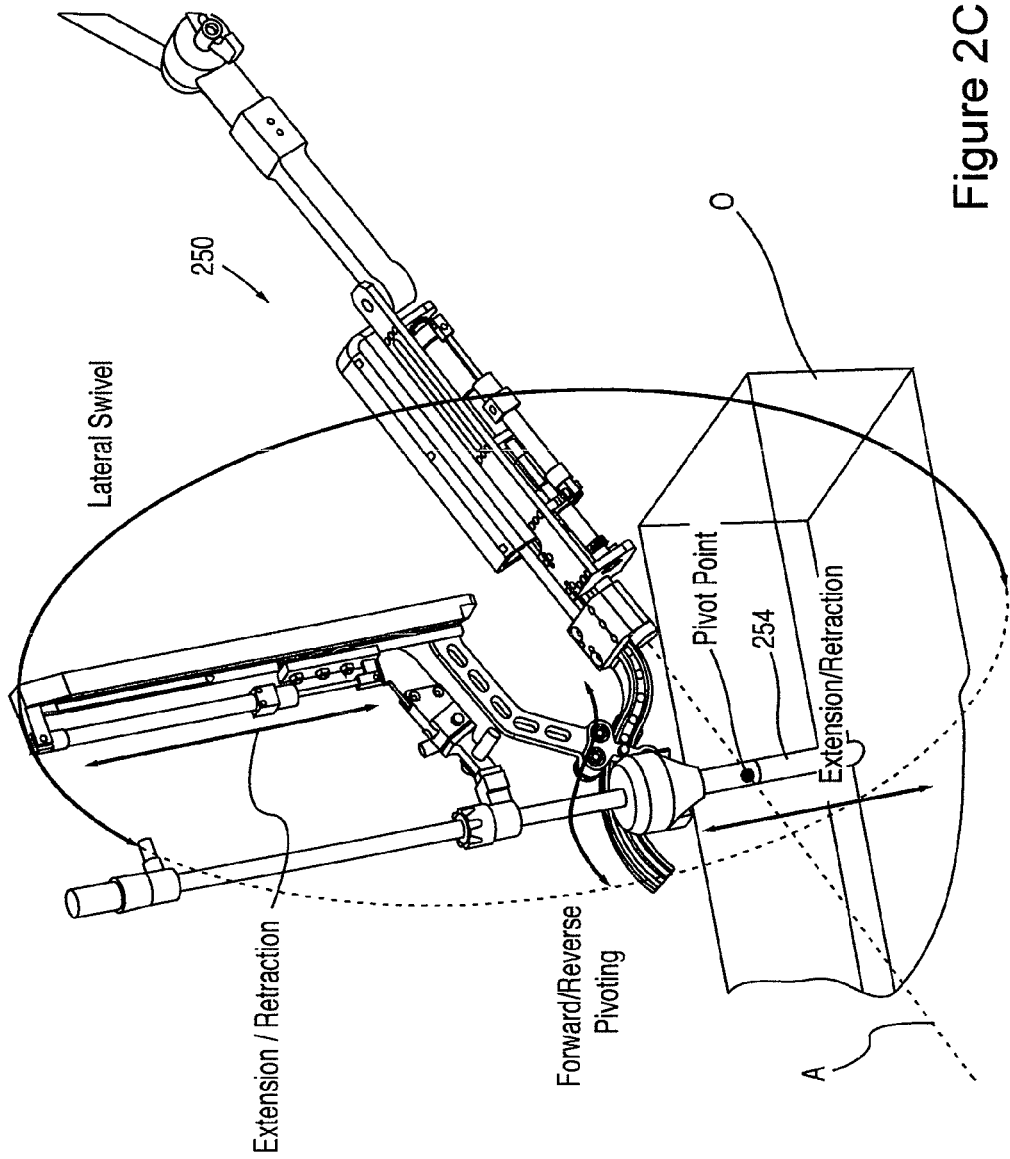
FIG. 2C is a side view of an exemplary slave portion that may be used in conjunction with the present invention.

FIG. 2C is a side view of an exemplary slave portion 250 that may be used in conjunction with aspects of the present invention. FIG. 12C, in particular, gives an overview of three exemplary macro degrees of freedom in one exemplary variation of the slave portion of the device. It should be noted that, while the exemplary degrees of freedom discussed herein are useful for certain applications, they are not meant to be exhaustive. Other degrees of freedom are within the scope hereof. Indeed, it is possible to modify the existing apparatus as described to encompass either additional or fewer degrees of freedom, as needed.

In FIG. 2C, one of the exemplary macro degrees of freedom shown is Forward/Reverse Pivoting of the instrument 254 and related components. Forward/Reverse Pivoting may allow instrument 254 to pivot about a central pivot point, such as Pivot Point shown in FIG. 2C. This particular pivoting degree of freedom is useful for, among other things, positioning the instrument 254 about a particular area of interest in an operational environment O. For example, the Forward/Reverse Pivoting degree of freedom can be used to position a tool, such as a scalpel, on the end of the instrument 254 in a position appropriate for the making of an incision. Alternatively, the Forward/Reverse Pivoting degree of freedom can be used for such operations as positioning tweezers on the end of the instrument 254 in a position appropriate for grasping a particular object (e.g., an organ or tissue).

In FIG. 2C, yet another of the exemplary macro degrees of freedom shown is Lateral Swivel of the instrument 254 and related components. The Lateral Swivel may allow instrument 254 to swivel about axis A. This particular degree of freedom is useful for, among other things, positioning the instrument 254 about a particular area of interest in an operational environment O. The Lateral Swivel degree of freedom can be used, for example, to position a scalpel on the end of the instrument 254 in a position appropriate for the making of an incision. Alternatively, Forward/Reverse Pivoting degree of freedom can be used for such operations as positioning tweezers on the end of the instrument 254 in a position appropriate for grasping a particular object (e.g., an organ or tissue).

In FIG. 2C, yet another of the exemplary macro degrees of freedom shown is Extension/Retraction of the instrument 254 and related components. Extension/Retraction may allow instrument 254 to be brought closer to or further away from the operational environment O. This particular degree of freedom may, for example, allow the instrument 254 to be retracted a safe distance from objects in the operating environment while it is repositioned using the Forward/Reverse Pivoting and Lateral Swivel motions. Once the instrument 254 has been repositioned, it may be brought back in contact with or in close proximity to the operational environment O using the Extension/Retraction degree of freedom.

Figure 2D:
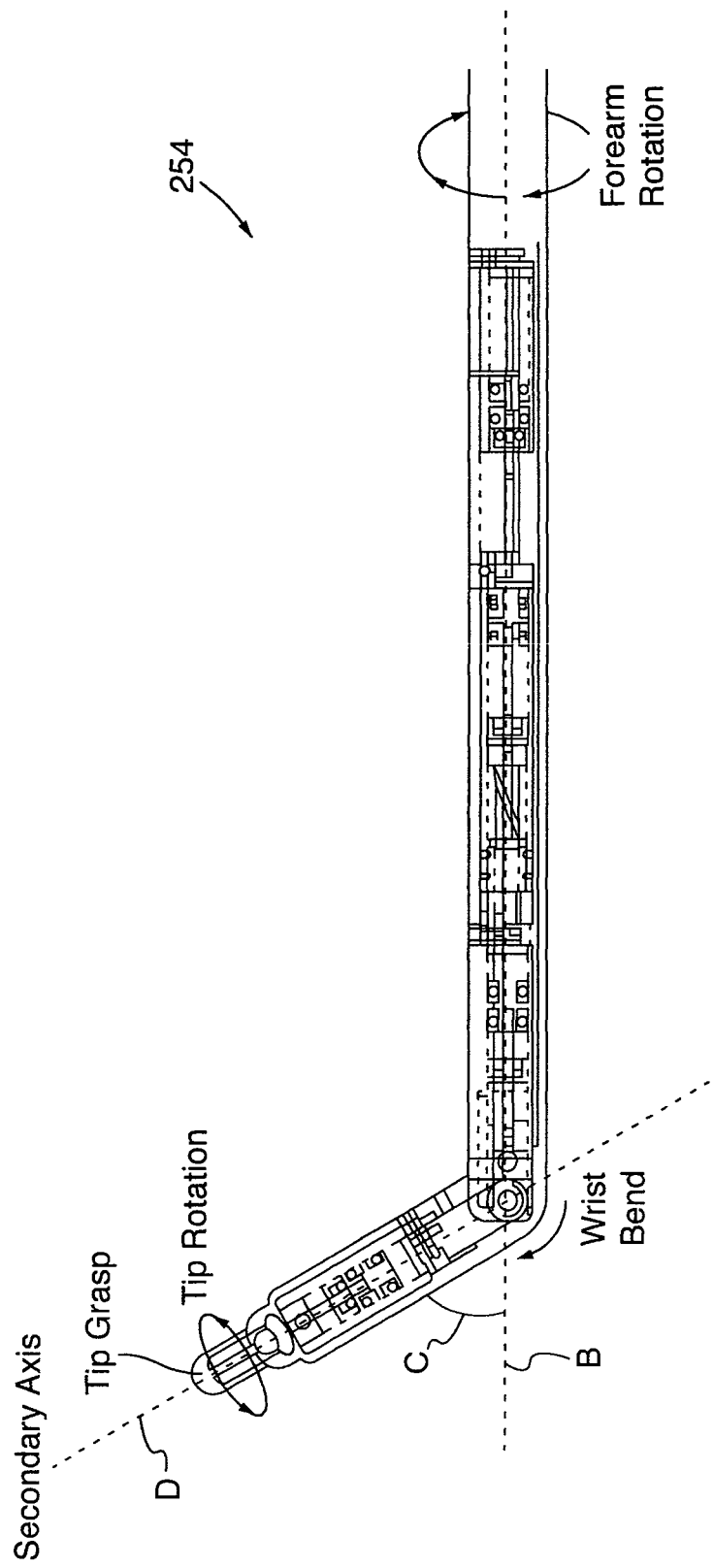
FIG. 2D is a close-up side view of an end of an exemplary tool that may be used in conjunction with aspects of the present invention.

FIG. 2D is a close-up side view of an end of an exemplary tool 254 that may be used in conjunction with aspects of the present invention. FIG. 2D also shows an overview of four exemplary micro degrees of freedom in an instrument and/or tool in accordance with aspects of the present invention. It should be noted that, while the exemplary degrees of freedom are useful for certain applications, they are not meant to be exhaustive. Other degrees of freedom are within the scope hereof. Indeed, it is possible to modify the existing apparatus as described to encompass either additional or fewer degrees of freedom, as needed. All such modifications should be considered within the scope hereof.

In FIG. 2D, one of the exemplary micro degrees of freedom shown is the Forearm Rotation of the instrument 254 and related components. Forearm Rotation may allow instrument 254 to rotate about a primary axis B of the instrument 254. This particular degree of freedom is useful for, among other things, positioning the instrument 254 about a particular area of interest in an operational environment O (see FIG. 2C). For example, the Forearm Rotation degree of freedom can be used to engage and/or position a tool, such as scalpel, on the end of the instrument 254, as appropriate for the making of an incision. Additionally, for example, the Forearm Rotation degree of freedom can be used to sweep a cutting motion with the scalpel on the end of the instrument 254. In another example, the Forearm Rotation degree of freedom can be used to locate a tool, such as tweezers, on the end of the instrument 254 in a position appropriate for grasping a particular object (e.g., an organ or tissue).

Also in FIG. 2D, another one of the exemplary micro degrees of freedom shown is the Wrist Bend of the instrument 254 and related components. Wrist Bend may allow instrument 254 to bend with respect to the primary axis B of the instrument 254 (e.g., about angle C), for example. This particular degree of freedom is useful for, among other things, positioning a portion of the instrument 254 and/or a tool about a particular area of interest in an operational environment O (see FIG. 2C). For example, the Wrist Bend degree of freedom can be used to position a scalpel on the end of the instrument 254 in a position appropriate for the making of an incision. For instance, the Wrist Bend degree of freedom can be used to sweep a cutting motion with a scalpel located at the end of the instrument 254. In another example, the Wrist Bend degree of freedom can be used to locate tweezers on the end of the instrument 254 in a position appropriate for grasping a particular object (e.g., an organ or tissue).

Further, in FIG. 2D, two additional exemplary micro degrees of freedom shown are Tip Rotation and Tip Grasp of the instrument 254 and related components. Tip Rotation may allow instrument 254 and/or tool to rotate about the primary axis B, or to rotate about a secondary axis D after bending a portion of instrument 254 relative to primary axis B. Tip Grasp may allow instrument 254 and/or tool to bend with respect to the primary axis of the instrument 254, for example, or to bend about a secondary axis formed after bending a portion of instrument 254 relative to primary axis. Further, for example, Tip Grasp may allow a relative bending or pivoting of two corresponding instrument or tool portions, e.g. pincher arms, to grasp or release an item. These particular degrees of freedom are useful for, among other things, positioning the instrument 254 and/or tool about a particular area of interest in an operational environment O (see FIG. 2C). For example, the Tip Rotation and Tip Grasp degrees of freedom can be used to engage or locate a scalpel on the end of the instrument 254 in a position appropriate for the making of an incision. Additionally, for example, the Tip Rotation and Tip Grasp degrees of freedom can be used to sweep a cutting motion with a scalpel on the end of the instrument 254. In another example, the Tip Rotation and Tip Grasp degrees of freedom can be used to locate tweezers on the end of the instrument 254 in a position appropriate for grasping or releasing a particular object (e.g., an organ or tissue).

Figure 3C:
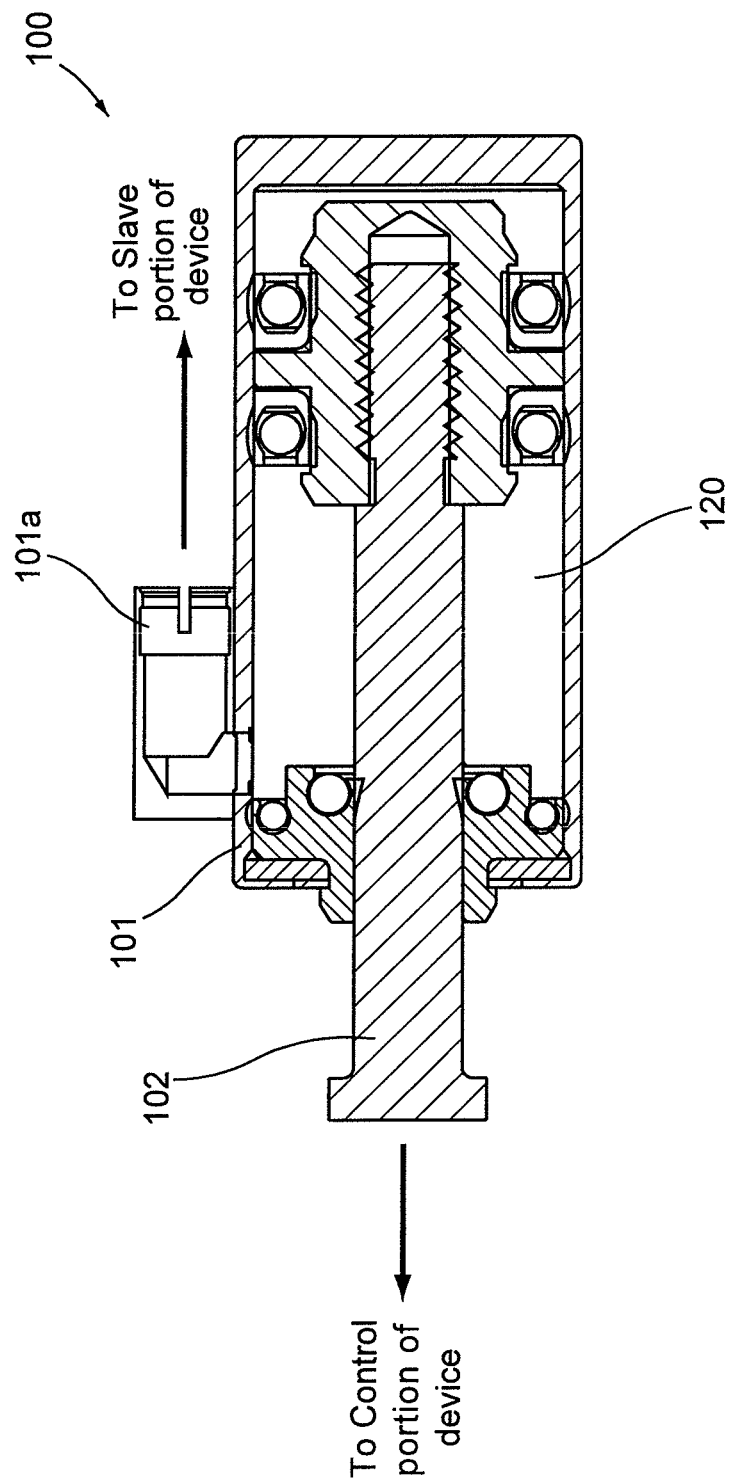
FIG. 3C is a cross sectional side view of the control cylinder of FIG. 3A in accordance with aspects of the present invention.

FIGS. 3A-3C illustrate an example of exemplary features of the control actuator 20 or the slave actuator 22 of FIG. 1, each generally defining a control cylinder 100, in accordance with aspects of the present invention. FIG. 3C shows a cross section of various features of a control cylinder 100, for example. As shown in FIGS. 3A, 3B and 3C, these features of the control cylinder include an outer cylinder 101, which may include a control cylinder shaft 102, for example. Upon receiving an input from the control portion 12 of the device 10 (FIG. 1), such as upon squeezing the thumb loop 54 of control unit 50 (see FIG. 2A) or the trigger loop 212 of control unit 200 (see FIG. 2B), a control cylinder 100 may be actuated through a series of levers and gears, from the retracted position shown in FIG. 3A to the extended position shown in FIG. 3B.

As shown in FIGS. 3A-3C, an exemplary control cylinder 100 includes an outer cylinder 101 and control cylinder shaft 102. The control cylinder shaft 102 is free to move within certain degrees of freedom with respect to the outer cylinder 101, and the shaft 102 may be in mechanical communication with the control portion 10 (FIG. 1). The movements of the control portion 12 (FIG. 1), described above, may cause control cylinder shaft 102 to move longitudinally with respect to the stationary outer cylinder 101, as shown in FIGS. 3A-3C. Fluid ports 101a and 101b may allow fluid communication with other aspects of the device to influence relative motion of the cylinder 101 and the shaft 102.

In one exemplary variation, hydraulic fluid 120 (FIG. 3C) is located in the inner cylinder 102. When the control portion 12 (FIG. 1) is moved as described above, the control cylinder shaft 102 moves. Hydraulic fluid 120 exits the outer cylinder 101, for example, through a port (e.g., 101b), creating a change in hydraulic pressure at a point in the distal end of the device. For example, hydraulic fluid 120 displaced from a slave cylinder enters the outer cylinder 101 through port 101b, thereby keeping a substantially constant volume of the hydraulic fluid 120 in the system. Generally, the control cylinder shaft 102 slides back and forth in the outer cylinder 101, as shown in FIGS. 3A and 3B. For example, in an aspect, when a part of the control portion 12 (FIG. 1) associated with the control cylinder 100 is moved to a limiting position in one direction, the control cylinder shaft 102 is in its retracted position (the position shown in FIG. 3A). In this way, among other things, the control portions with a single control cylinder or control portions with multiple control cylinders use the control cylinder 100 to passageway the mechanical force from the user, as received by the control portion 12, to the application or slave portion 16 of the device 10 (see FIG. 1). Generally, the slave portion 16 may include slave actuators 22 that attenuate the received hydraulic input and generate an output to drive an end effecter on the device 10 (FIG. 1).

For example, an end effecter may include, but is not limited to, mechanical grippers, lever arms, cutting tools, grasping tools and any other suitable devices. The mechanical force generated at the slave portion 16 (FIG. 1) can be used in any number of suitable ways by the slave portion of the devices. For example, the control portions with a single control cylinder or control portions with multiple control cylinders may be used to conduct surgical procedures, move objects or to mechanically provide force for any suitable number of applications. As shown in FIG. 1, the control portions with a single control cylinder or control portions with multiple control cylinders may be coupled to various surgical apparatus (e.g., clamps, shears, needles) for performing a surgical operation.

Control cylinders 100, such as those shown in FIGS. 3A and 3B, can be used to drive complex mechanical systems, such as in conjunction with other control cylinders. For example, one control cylinder may be actuated by the control system of FIG. 2A and communicate fluid, ultimately, with one or more other control cylinders in the slave portion of the device. Coupling of the hydraulics between the control cylinders in the master and the slave portions of the device may be accomplished by a variety of methods and features, including by directly connecting hydraulic lines, and by use of a number of suitable connectors or crimpers, valves and other features.

Figure 4A:
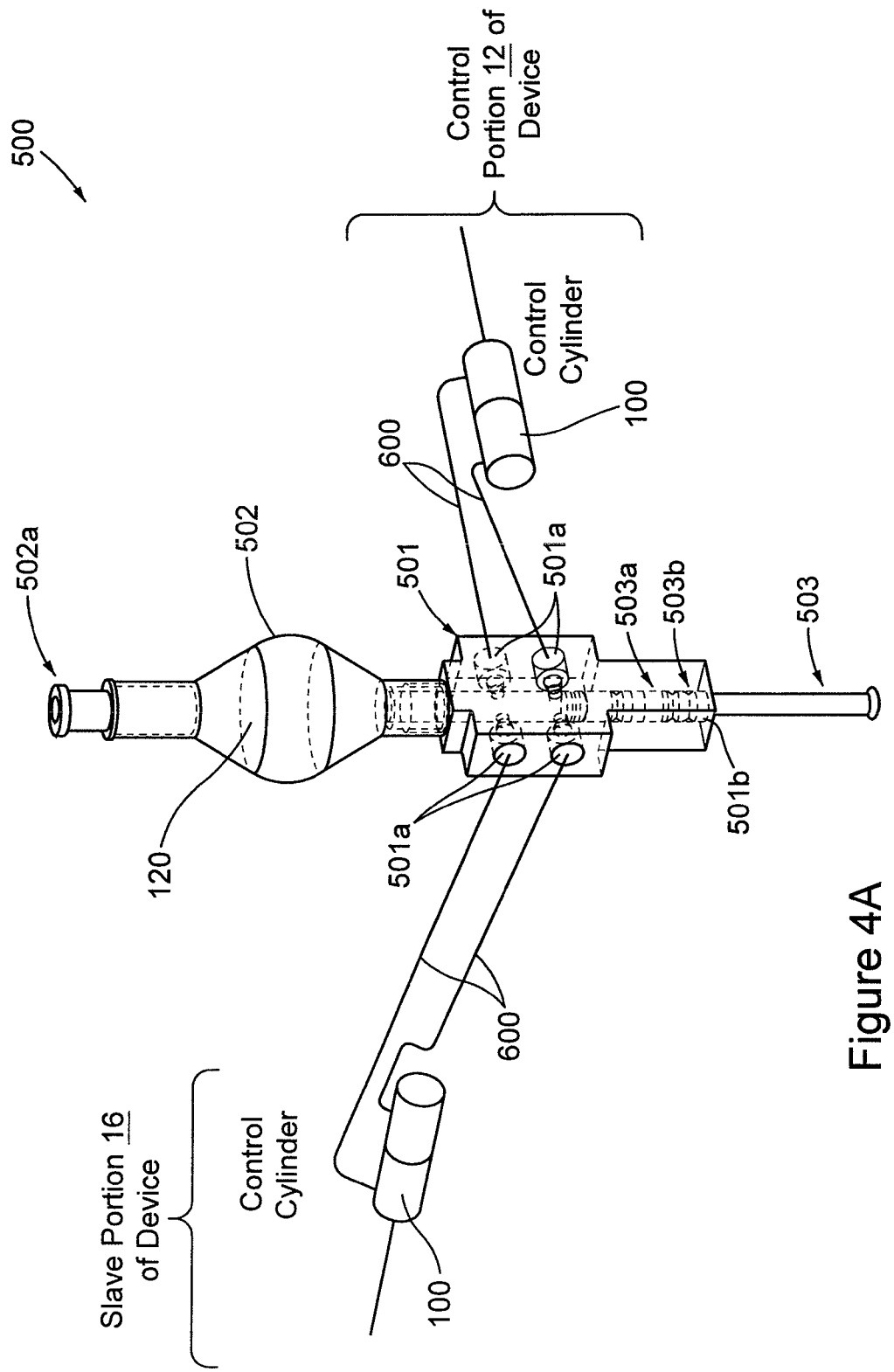
FIG. 4A is a perspective view of an exemplary spool valve used to control fluid communication with two control cylinders and other components in accordance with aspects of the present invention.
Figure 4B:
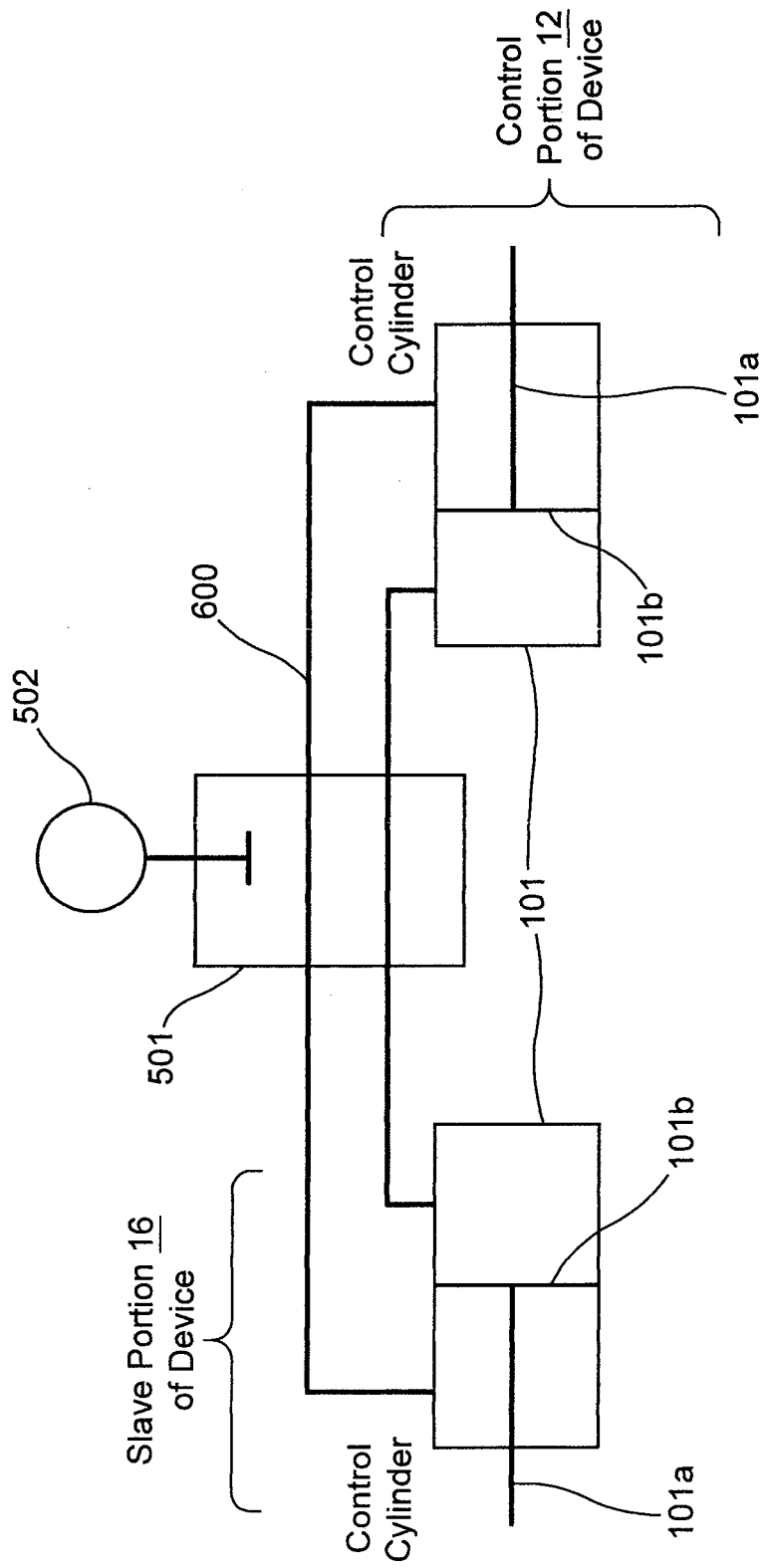
FIG. 4B is a schematic diagram of the hydraulic system associated with the exemplary spool valve of FIG. 4A.

FIG. 4A is a diagram of an aspect of a spool valve 500 used in spool valve system 18, or hydraulic system 14 (see FIG. 1), to control fluid communication between two control cylinders, and optionally between other additional components. FIG. 4B is a schematic diagram of the hydraulic system associated with the exemplary spool valve 500 of FIG. 4A. As shown in FIGS. 4A and 4B, the exemplary spool valve 500 may connect control cylinders in the control portion 12 of the device 10 with control cylinders in the slave portion 16 of the device 10 (see FIG. 1). Although FIGS. 4A and 4B show a specific orientation of the control and slave portions of the device with respect to the spool valve, it is to be understood that this configuration is merely exemplary and could be altered or reversed as needed. FIGS. 4A and 4B also show the exemplary spool valve 500 connecting only two control cylinders 100. It is to be further understood that any suitable number of control cylinders may be connected with the exemplary spool valve 500. Further, any suitable number of control cylinders in slave portions of the device may be connected to any suitable number of control cylinders in the control portion of the device via one or more of the exemplary spool valve 500 or any one or any combination of the other exemplary spool valves discussed herein.

As shown in FIG. 4A, the exemplary spool valve 500 can have a main body portion 501 with four ports 501a that connect to control cylinders 100 via hydraulic lines 600, and a spool-receiving opening 501b for receiving a spool 503. Although only four ports 501a are shown, it is to be understood that any suitable number of ports 501a may be provided on the exemplary spool valve 500 for fluid communication to other devices, including additional control cylinders. The ports 501a may include any suitable type of fluid connection that allows fluid communication between the main body portion 501 and the hydraulic lines 600. For example, the ports 501a may include retaining mechanisms that fix the ends of the hydraulic lines 600, such that a fluid-tight seal is provided between the hydraulic lines 600 and the main body portion 501 of the exemplary spool valve 500. Alternatively, the hydraulic lines 600 may connect to the main body portion 501 through a socket and connector mating system, for example. In this case, the socket may be on either the hydraulic line or on the main body portion 501. It will be appreciated by those skilled in the art that many additional connection mechanisms may also be suitable if their use is consistent with aspects of the present invention.

Hydraulic fluid 120 used within the spool valve 500 and with other exemplary aspects of the present invention may be any suitable hydraulic fluid. This suitable hydraulic fluid 120 may comprise, for example, any number of suitable oils, such as mineral oil. The hydraulic fluid 120 may also be a fluid that is medically benign, such as saline or water.

The hydraulic lines 600 may comprise a variety of materials, including plastics, rubbers and/or may include various fibers or metal weavings for additional structural support, for example, to maintain a substantially constant volumetric cross-section. The hydraulic lines 600, corresponding control cylinders, and the spool valves may be of any suitable size and have any suitable inner and outer diameters for the particular applications. It is noted that drawings represented herein of components relating to various aspects of this invention are not necessarily to scale. In fact, the components and principles articulated here may operate on several different size scales alternatively or contemporaneously.

The exemplary spool valve 500 may include a reservoir 502 for storing hydraulic fluid 120. Generally, fluid 120 in the reservoir 502 may be used to replenish the fluid 120 in the hydraulic lines 600 or other hydraulic portions of the device as it is lost through use or for other reasons. For example, the hydraulic fluid 120 may be lost both during use and while the device is dormant (e.g., when it is being stored for future use) for a number of reasons. These reasons could include evaporation through the walls of the hydraulic lines 600, evaporation or leakage at other locations in the device (e.g., at joints or connections) or through malfunction and/or rupture of any of components of the device. In addition or alternative to the above, it may be advantageous to drain the hydraulic fluid 120 from the system and replace the hydraulic fluid through the reservoir 502.

The reservoir 502 may be flexible or made from flexible materials including rubber, elastomers, various polymers and plastics, as well as latex. Alternatively, the reservoir 502 may be rigid and may include metals, ceramics or other rigid materials. It may also be advantageous for the reservoir 502 to include some type of clear material or a clear portion, such as a window, in order to allow the level of hydraulic fluid in the reservoir to be easily ascertained. However, the reservoir 502 need not be clear nor have a clear portion. In addition, sensors or various other suitable types of meters or detectors may be used to track or obtain the level of hydraulic fluid in the reservoir 502. Such sensors may be optical, mechanical, or use another suitable mechanism.

The reservoir 502 may also contain a fill port 502a, such as, but not limited to, a port located at the top of the spool valve 500, as shown in FIG. 4A. The fill port 502a may allow the hydraulic fluid 120 to be re-filled, replenished or replaced. The fill port 502a may alternatively be located on other suitable positions such that it provides access to the reservoir 502. The fill port 502a may include an opening with a cap or plug, as shown in FIG. 4A, or it may comprise a more complicated mechanism. For example, fill port 502a may contain a plurality of connections, plugs, caps or ports. The fill port 502a may be independently sealable, as shown in FIG. 4A, or it may be connected to a pump, fluid supply line or other feature or device.

The exemplary spool valve 500 shown in FIG. 4A also contains a spool 503 that may, among other things, control fluid communication between the control cylinders on either side of the exemplary spool valve 500. The spool 503 may contain various features for obtaining fluid-tight seals to prevent cross communication, or other communication, of fluids within the spool 503, or among other components in fluid communication with the spool 503. For example, in an aspect, spool valve 500 may include a series of seal tubes 503a and O-rings 503b. The seal tubes 503a and O-rings 503b may include any suitable material for providing a fluid-tight seal. For example, the seal tubes 503a and O-rings 503b may comprise rubber, polymer or plastic. The seal tubes 503a and O-rings 503b may be completely impermeable to fluid, semipermeable or selectively permeable. In addition, the spool 503 may contain other features, such as passageways or filters, that allow fluid communication among different portions of the spool 503.

Figure 5A:
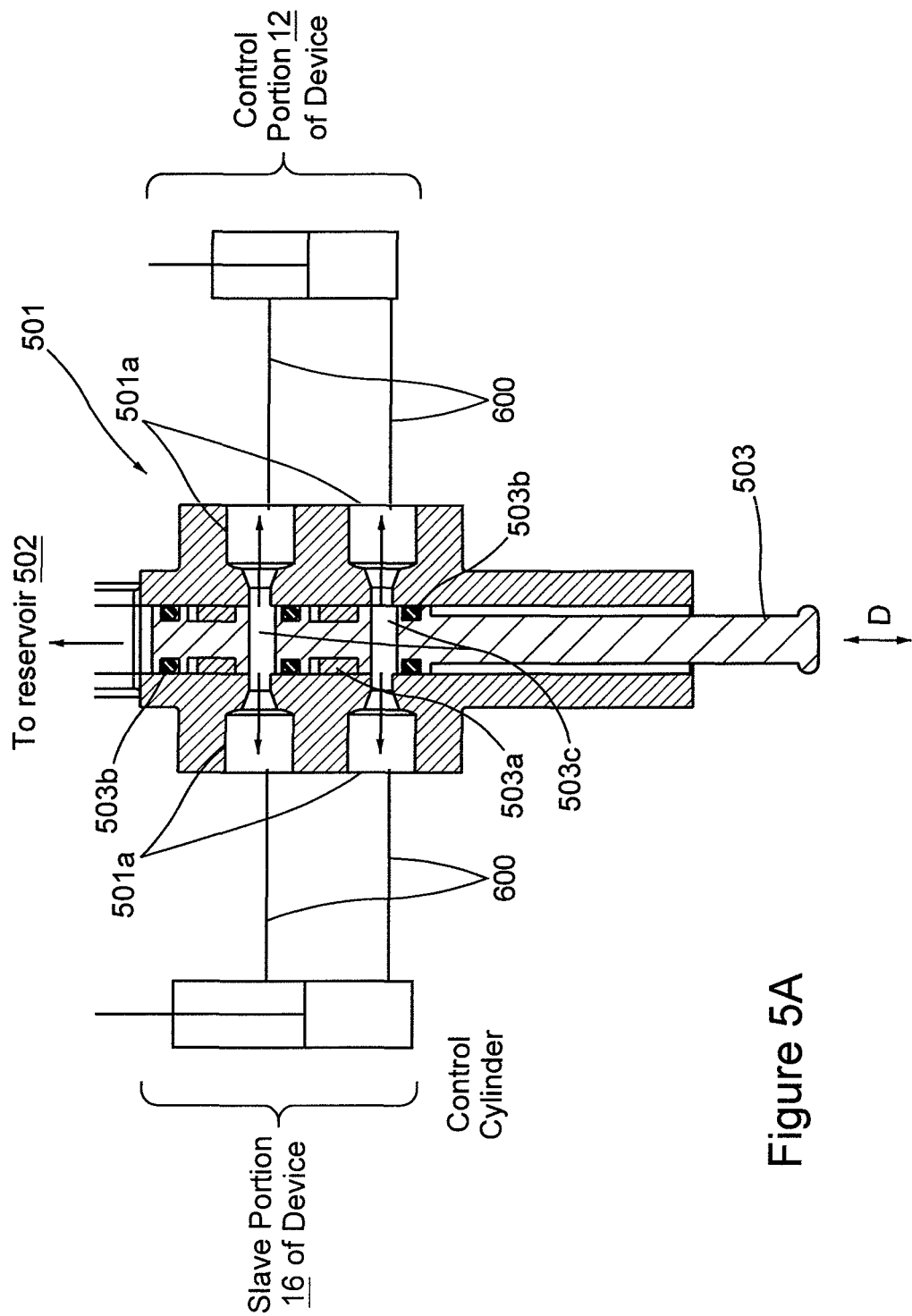
FIG. 5A is a close-up, partial cross-sectional side view of an aspect of the exemplary spool valve of FIG. 4A positioned in a use mode.
Figure 5B:
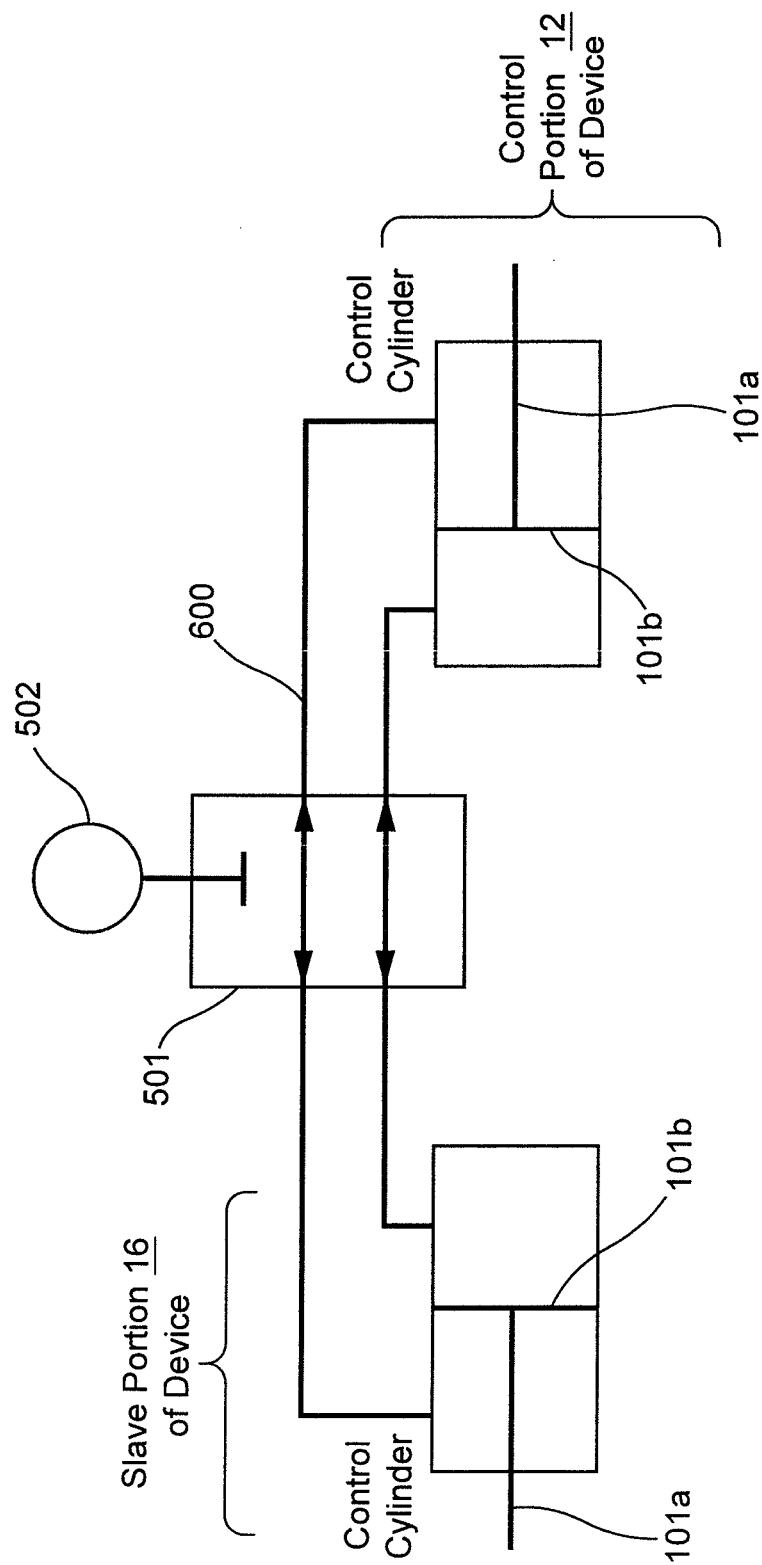
FIG. 5B is a schematic diagram of the hydraulic system associated with the exemplary spool valve of FIG. 5A in the use mode.

FIG. 5A shows a close-up view of the exemplary spool valve 500 in a use mode, in accordance with aspects of the present invention. FIG. 5B is a schematic diagram of the hydraulic system associated with the exemplary spool valve of FIG. 5A in use mode. As shown in FIG. 5A, the spool 503 may include two passageways 503c that allow fluid communication between corresponding fluid lines 600 on either side of the spool 503 (note that FIG. 5A shows passageways cut all the way through the valve stem, it is to be understood that the passageways do not sever the valve stem). While FIG. 5A shows that the passageways 503c may be a channel, it is within the scope hereof that other suitable features for allowing passage of a fluid may be implemented, such as a valve. FIG. 5B indicates that fluid may flow in either direction through these passageways in the use mode. Also, as noted in FIG. 5B, in use mode, the spool 503 is positioned such that no fluid communication occurs between the cylinders or hydraulic lines 600 and the reservoir 502. Although two passageways 503c are shown in FIG. 5A, it is to be understood that any suitable number of passageways are possible, depending on the particular application. The spool valve 503 may also include devices and features for sealing off or preventing fluid communication between the passageways 503c, or between one or more passageways 503c and the reservoir 502. These devices and features may include O-rings 503b, valves or stoppers, among other features. The devices and features may comprise rubber, elastomer, polymer, plastic or combinations of any suitable material. In some aspects, the devices and features are not permeable to the hydraulic fluid; however, they may be permeable to other media. In another aspect, the devices and features may be semi-permeable and/or porous, in certain variations, even to hydraulic fluid.

In use mode, as shown in FIG. 5A, hydraulic fluid communication among various portions of the device may be limited by the construction of the spool 503. In use mode, the spool 503 may be configured to prevent fluid communication between the reservoir 502 and the slave 16 and control portion 12 of the device, as best shown in FIG. 5B. Isolating the reservoir 502 from the hydraulically active portions of the device (e.g., the slave and control portions), may allow hydraulic pressure from the control cylinders in the control portion of the device to actuate control cylinders in the slave portions of the device, without a release of pressure occurring to the reservoir 502.

The exemplary spool valve 500 (FIG. 4A) may be placed in use mode by moving the spool 503 axially in the direction D, as shown in FIG. 5A, or otherwise in the appropriate direction to align the flow passageways 503c in the spool with the ports 501A in the valve body 501. The spool 503 and the passageways 503c may have any suitable construction such that the use mode is accessed by some motion of the spool 503. For example, the passageways 503c in the spool could be constructed so that use mode is accessed by direct axial-length motion (axis D) or by rotating the spool 503 around axis D, such that rotation aligns the passageways 503c and ports 501a or produces suitable axial motion in direction D for alignment. Alternatively, it is within the scope hereof that the spool valve and the passageways could be constructed such that use mode is accessed by moving the spool 503 laterally, or in the direction parallel to the flow of hydraulic fluid through the passageways 503c. It is also within the scope hereof that the spool valve and the passageways 503c may be constructed such that use mode is accessed when the spool 503 is put through a more complicated motion (e.g., one that involves some combination of vertical, lateral and/or rotational motion).

Figure 6A:
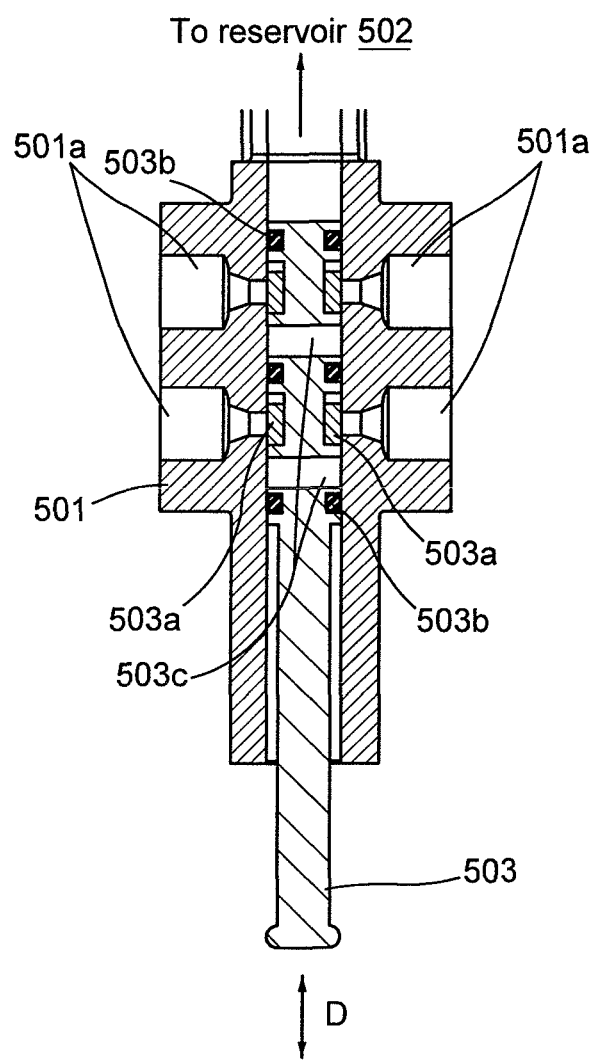
FIG. 6A is a close-up, partial cross-sectional side view of the exemplary spool valve 500 of FIG. 4A positioned in a brake mode.
Figure 6B:
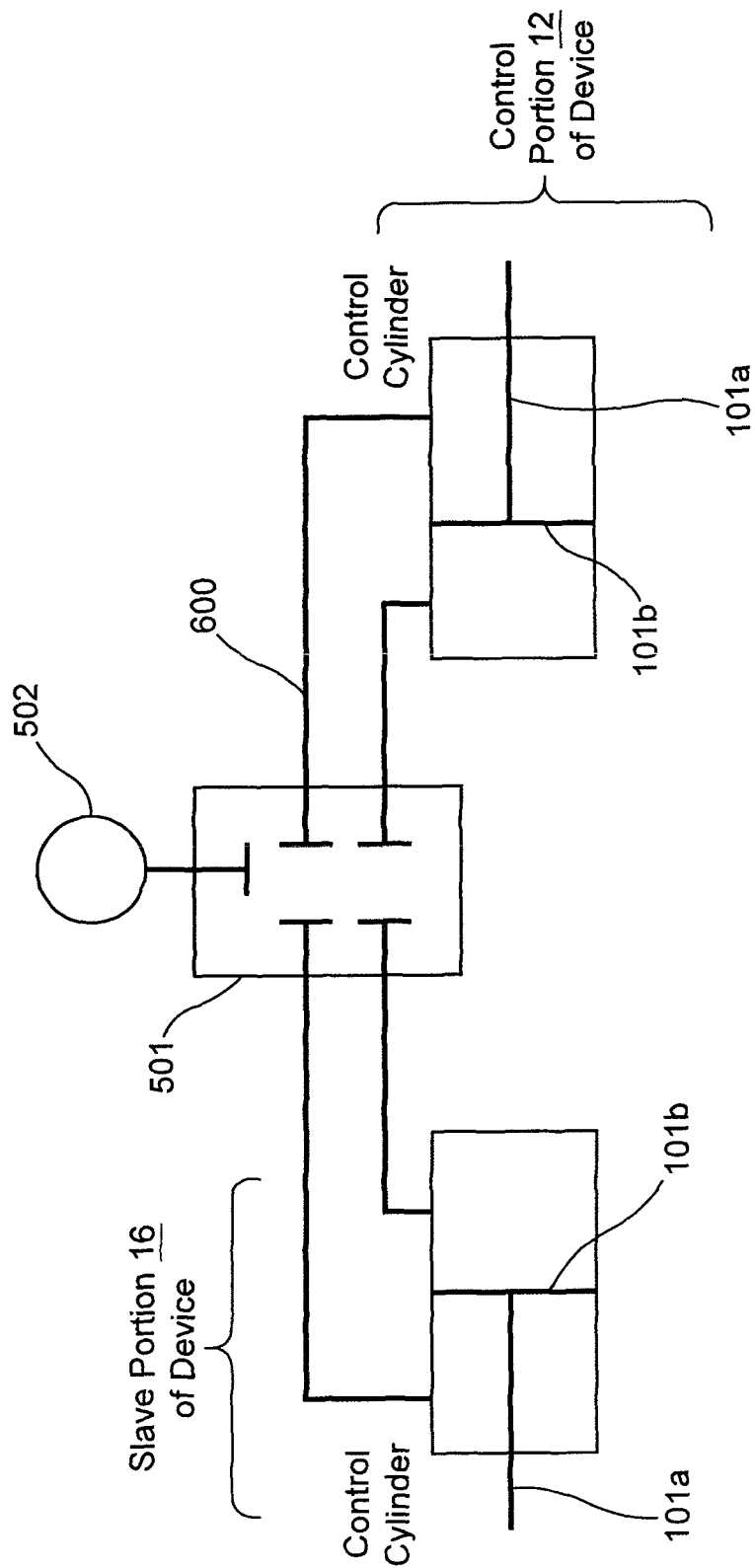
FIG. 6B is a schematic diagram of the hydraulic system associated with the exemplary spool valve of FIG. 6A in the brake mode.

FIG. 6A shows a close-up view of the exemplary spool valve 500 in a brake mode, in accordance with aspects of the present invention. FIG. 6B is a schematic diagram of the hydraulic system associated with the exemplary spool valve of FIG. 6A in brake mode. As shown in FIG. 6A, in brake mode, the spool 503 may be positioned so that the passageways 503c that allow fluid communication between fluid lines 600 on either side of the spool 503 in use mode are not in fluid communication with the hydraulic lines 600 via ports 501a. As also shown in FIG. 6A, the spool valve 503 may include devices and features for sealing off each of the connections to the hydraulic lines 600. In FIG. 6A, the devices and features for sealing off the hydraulic lines 600 may include seal tubes 503a, such as O-rings, that are sized to overlap to respective openings to ports 501a that connect the hydraulic lines 600 to the exemplary spool valve 500. Seal tubes 503a may comprise such materials as rubber, elastomer, polymer or other elastic material. However, the seal tubes 503a may also include other suitable materials for creating a fluid-tight seal, including combinations of materials already mentioned, as well as other suitable materials. In some aspects, the seal tubes 503a may not be permeable to the hydraulic fluid 120; however, they may be permeable to other media. In some aspects, seal tubes 503a may be semi-permeable and/or porous. The seal tubes 503a generally serve as a barrier to fluid flow from the hydraulic lines 600, although they may serve other purposes and also allow limited flow of the fluid from the hydraulic lines 600.

One of the uses of brake mode for the spool valve 500 may be to alter, prevent, hinder or dampen user actuation of the control cylinders in the slave portions of the device when actuation of the slave portion control cylinders is not necessary and/or may possibly be detrimental. For example, during surgery it may be necessary to pause to allow the patient to reach a stable condition, for necessary tools and/or resources (e.g., medications) to be delivered, or for the surgeon to simply take a break. In addition, multiple surgeons may be present for performing different aspects of a single procedure. When a new surgeon takes over the operation, it may be necessary to lock the device in brake mode so that inadvertent contact with the control portion of the device in the changeover does not cause damage to the device, injure the patient, or cause other detrimental conditions in the operating theater. In addition, it may be necessary, in the course of an operation, to use tools that perform other functions requiring stopped motion. In each of these situations, as well as others, it may be necessary to immobilize the tools used by the device temporarily so that no damage occurs to the patient or any other aspect of the operation while the device is not in use. Brake mode can interrupt the hydraulic connections between the control portions and the slave portions of the device to prevent transfer of an input to the control portion from being translated to an output at the slave portion, so as to prevent patient injury or other damage from being caused by inadvertent actions on the control portion of the device.

As shown in FIG. 6A, the exemplary spool valve 500 can be placed in brake mode by moving the spool 503 in the direction D axially, for example, so as to align the seal tubes 503a on the spool with the ports 501a in the valve body 501 (e.g., to the position shown in FIG. 6A, from the position shown in FIG. 5A). However, it is to be understood that the spool valve 500 could be constructed, within the context hereof, such that brake mode is accessed when the spool 503 is in another position. Further, the spool 503, the ports 501a, the passageways 503c and the seal tubes 503a could have any suitable alternative construction such that brake mode may be accessed by some other motion of the spool 503. For example, the passageways 503c and the seal tubes 503a in the spool could be constructed so that brake mode is accessed by rotating the spool 503 about its axis (e.g., so that the passageways 503c are out of alignment with ports 501a, thereby preventing flow of fluid therethrough; or by screw-type motion producing displacement of the spool 503 in direction D). Alternatively, it is within the scope hereof that the spool 503, passageways 503c, and the seal tubes 503a could be constructed such that the brake mode may be accessed by moving the spool 503 laterally, or in the direction parallel to the flow of hydraulic fluid through the passageways 503c. It is also within the scope hereof that the spool valve and the passageways 503c may be constructed such that brake mode is accessed when the spool 503 is put through a more complicated motion (e.g., one that involves some combination of vertical, lateral and/or rotational motion).

Figure 7A:
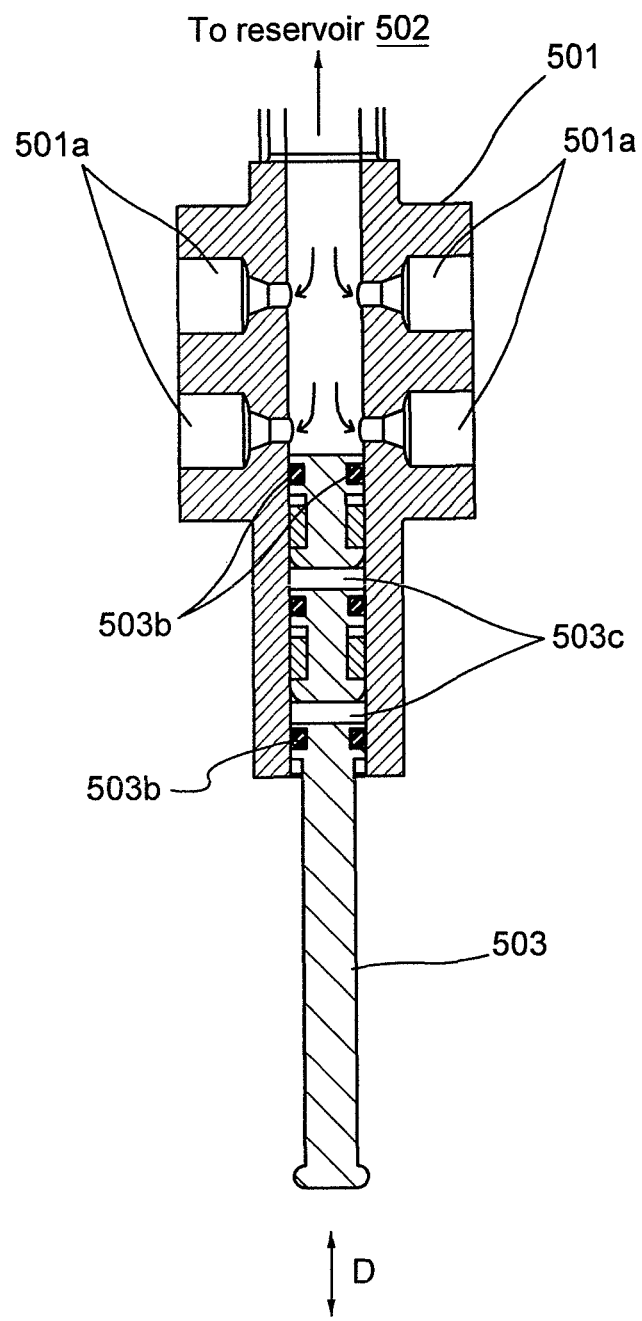
FIG. 7A is a close-up, partial cross-sectional side view of the exemplary spool valve 500 of FIG. 4A positioned in a storage mode.
Figure 7B:
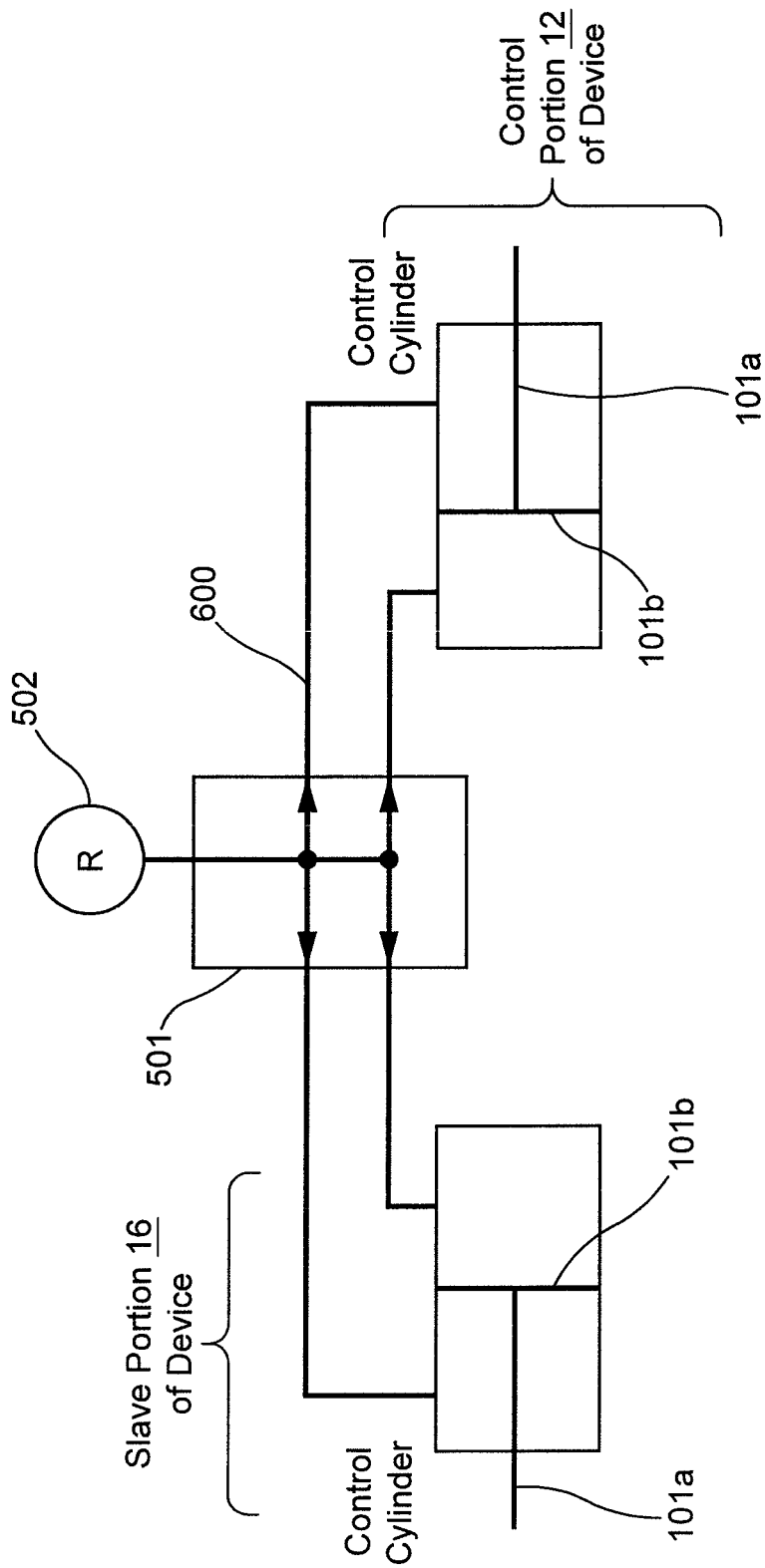
FIG. 7B is a schematic diagram of the hydraulic system associated with the exemplary spool valve of FIG. 7A in storage mode.

FIG. 7A shows a close-up view of the exemplary spool valve 500 in storage mode in accordance with aspects of the present invention. FIG. 7B is a schematic diagram of the hydraulic system associated with the exemplary spool valve of FIG. 7A in storage mode. As shown in FIGS. 7A and 7B, in storage mode, as in brake mode, the spool 503 is positioned so that the passageways 503c, which allow fluid communication between fluid lines 600 on either side of the spool 503 in use mode, do not allow communication via the ports 501*a* through the hydraulic lines 600. As also shown in FIGS. 7A and 7B, in storage mode, each of the hydraulic lines 600 is in fluid communication with both the reservoir 502 and with each of the hydraulic lines 600. Thus, the spool 503 is in such a position as to render each of the control cylinders in the slave 16 and control portions 12 of the device 10 (FIG. 10) to be in communication with the reservoir 502. This position can have the effect of individually de-coupling each of the cylinders in the control portion of the device from its respective control cylinder in the slave portion of the device. Unlike in brake mode, however, this de-coupling may be accomplished by placing all of the control cylinders of the device in fluid communication with each other and with reservoir 502, thereby creating a state of equilibrium.

One of the purposes of storage mode, among others, may be to prevent user actuation of the control cylinders in the slave portions of the device when actuation of the slave portion control cylinders is not necessary and/or possibly detrimental. Some of the situations discussed with reference to the uses of brake mode above also may apply to storage mode. One benefit of fluidly communicating each of the control cylinders and hydraulic lines with the reservoir 502 is to allow replenishment of hydraulic fluid in the system, such as may be lost due to evaporation or leakage. This replenishment can be especially useful if the hydraulic system includes any features semi-permeable to the hydraulic fluid that, for example, may allow evaporation. During storage mode, the device may lie dormant for long periods of time, making evaporation of the hydraulic fluid a potentially more pressing issue than in any other mode. Since the use mode and the brake mode are generally employed for relatively brief periods, the amount of evaporation and/or fluid loss due to leakage may be slight in these modes.

In storage mode, as shown in FIG. 7A, hydraulic fluid communication between various portions of the device may be equalized by the placement of the spool 503 relative to the ports 501*a*, such that all ports 501*a* are in fluid communication with each other and with reservoir 502. More particularly, each control cylinder of the slave 16 and control portion 12 of the device 10 may be in fluid communication with each of the other control cylinders of the device when the exemplary spool valve 500 is in storage mode. This fluid communication can prevent inadvertent movements in a control cylinder in the control portion of the device since an increase in hydraulic pressure is not directly transferred to the corresponding control cylinder in the slave portion of the device, as the movement causes hydraulic pressure to be distributed throughout the system and to the reservoir 502. In some aspects, for example, if the reservoir 502 is open to ambient pressure (or contains an opening or connection to ambient pressure), then the increase in hydraulic pressure can be dissipated through the reservoir 502. In storage mode, generally neither the O-rings 503*c* nor the seal tubes 503*a* of the spool 503 prevent fluid communication between the reservoir 502 and the slave and control portion of the device. Thus, placing each of the control cylinders of the device in fluid communication with each other and the reservoir 502 can prevent hydraulic pressure from the control cylinders in the control portion the device from actuating control cylinders in the slave portions of the device.

The exemplary spool valve 500 can be placed in storage mode by moving the spool 503 axially along the direction D, or in another appropriate direction, depending on configuration, within valve body 501 so as to prevent seals in the spool from obstructing the fluid communication between the ports 501*a* and the reservoir 502 (e.g., to the position shown in FIG. 7A). However, it is to be understood that the spool valve 500 could be constructed, within the scope hereof, such that storage mode is accessed when the spool 503 is in another position. For example, the spool 503 could be constructed with a region that has additional, connected passageways that serve to connect each of the ports 501*a* to the reservoir 502. Further, the spool 503 could have any suitable alternative construction such that storage mode is accessed by some other motion of the spool 503. For example, the spool could be constructed so that storage mode is accessed by rotating the spool 503 about its axis. It is within the scope hereof that the spool 503 could be constructed such that storage mode is accessed by moving the spool 503 laterally, or in the direction parallel to the flow of hydraulic fluid through the passageways 503*c*.

Figure 8:
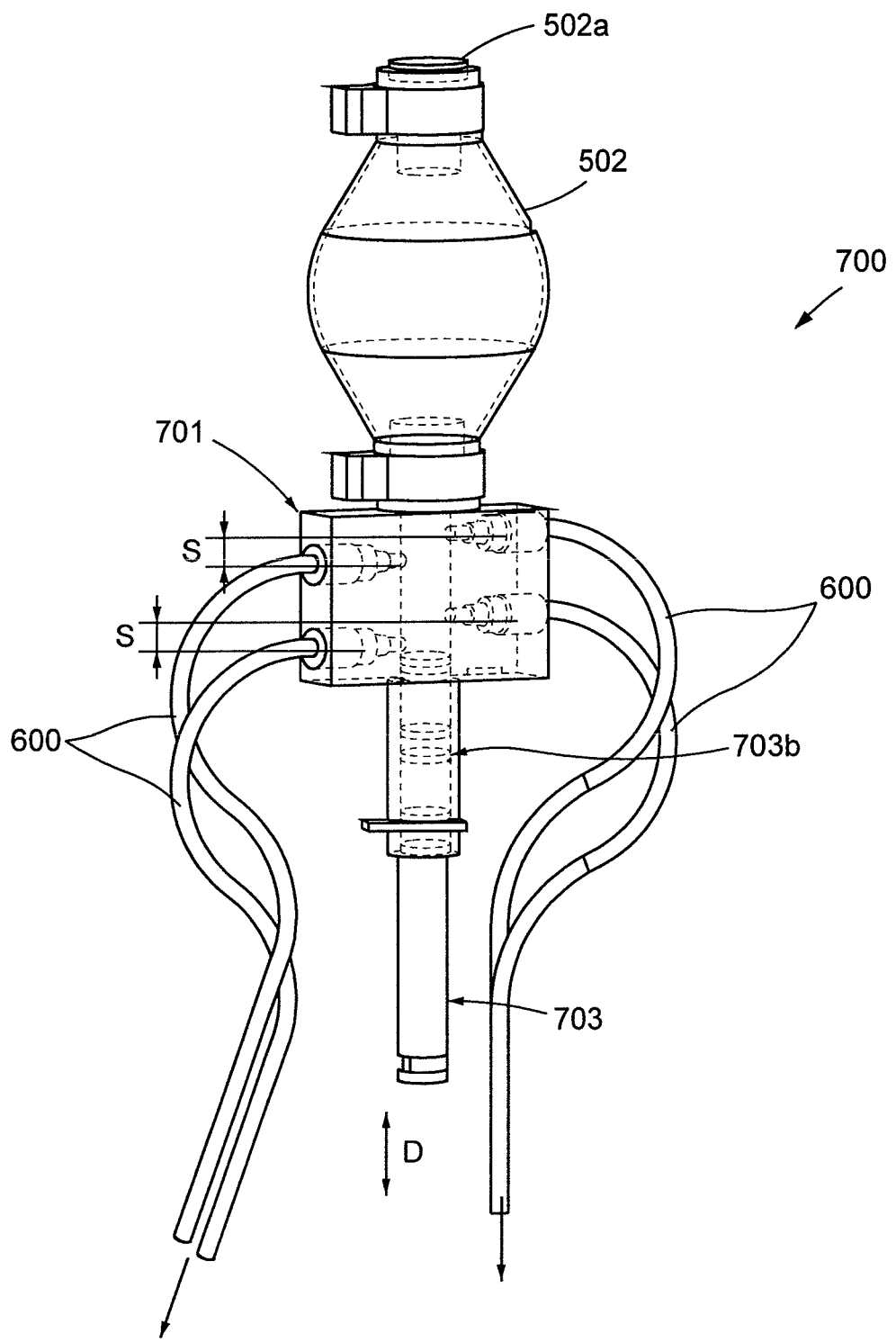
FIG. 8 is a side view of an exemplary spool valve used to control fluid communication with two control cylinders and other components in accordance with aspects of the present invention.

FIG. 8 is a diagram of another variation of an exemplary spool valve 700 used to control fluid communication with two control cylinders and other components, in accordance with aspects of the present invention. Spool valve 700 may connect control cylinders in the control portion of the device with control cylinders in the slave portion of the device, for example, similarly to the connections shown in FIG. 5A for the exemplary spool valve shown therein. Although FIG. 8 shows a specific orientation of the control and slave portions of the device with respect to the spool valve 700, it is to be understood that this configuration is merely exemplary and could be altered, or reversed, for example. FIG. 8 also shows the exemplary spool valve 700 connecting two ports. It is to be further understood that any suitable number of control cylinders may be connected with the exemplary spool valve 700. Further, any suitable number of control cylinders in the slave portion of the device may be connected to any suitable number of control cylinders in the master/control portion of the device via the exemplary spool valve 700 or any of the other exemplary spool valves discussed herein.

As shown in FIG. 8, the exemplary spool valve 700 has a main body portion 701 with four ports 701*a* that connect to the control cylinders via hydraulic lines 600. Although only four ports 701*a* are shown, it is to be understood that any suitable number of ports 701*a* may be provided on the exemplary spool valve 700 for fluid communication to other devices, including additional control cylinders. The exemplary spool valve 700 of FIG. 8 differs from the exemplary spool valve 500 of FIG. 5A in that each port 701*a* is staggered with respect to its corresponding port 701*a* on the opposite side of the main body portion 701 by staggering amount S, as shown in FIG. 8. Among other advantages, staggering the ports 701*a*, as shown in FIG. 8, may allow the use of O-rings 703*b* (not shown in FIG. 8) to cap or seal each of the hydraulic lines 600 connected to the ports 701*a*. The use of O-rings may be in lieu of seal tubes 503*a* used in the exemplary spool valve 500 for similar purposes, as shown in FIG. 6A. In FIG. 8, using O-rings 703*b* instead of seal tubes 503*a* (FIG. 5A) may permit higher hydraulic pressures to be used in the hydraulic lines 600 and throughout the entire device. For example, certain types of O-rings 703*b* can be used to seal the ports 701*a* at pressures of up to 3000 psi, while seal tubes 503*a* of FIG. 5A are typically used at substantially lower pressures.

The ports 701*a* may include any suitable type of fluid connection that allows fluid communication between the main body portion 701 and the hydraulic lines 600. For example, the ports 701*a* may contain crimping mechanisms that fix the ends of the hydraulic lines 600 such that a fluid-tight seal is provided between the hydraulic lines 600 and the main body portion 701 of the exemplary spool valve 700. Alternatively, the hydraulic lines 600 may connect to the main body portion 701 through a socket and connector mating system. In this case, the socket may be on either the hydraulic line or on the main body portion 701. It will be appreciated by those skilled in the art that many additional connection mechanisms are also suitable so long as their use is consistent with aspects of the present invention.

The exemplary spool valve 700 also may contain a reservoir 502 for storing hydraulic fluid. This reservoir may be substantially similar to the reservoir 502 shown in FIG. 5A, or it may have additional modifications for operation at higher or lower hydraulic pressures.

Figure 9:
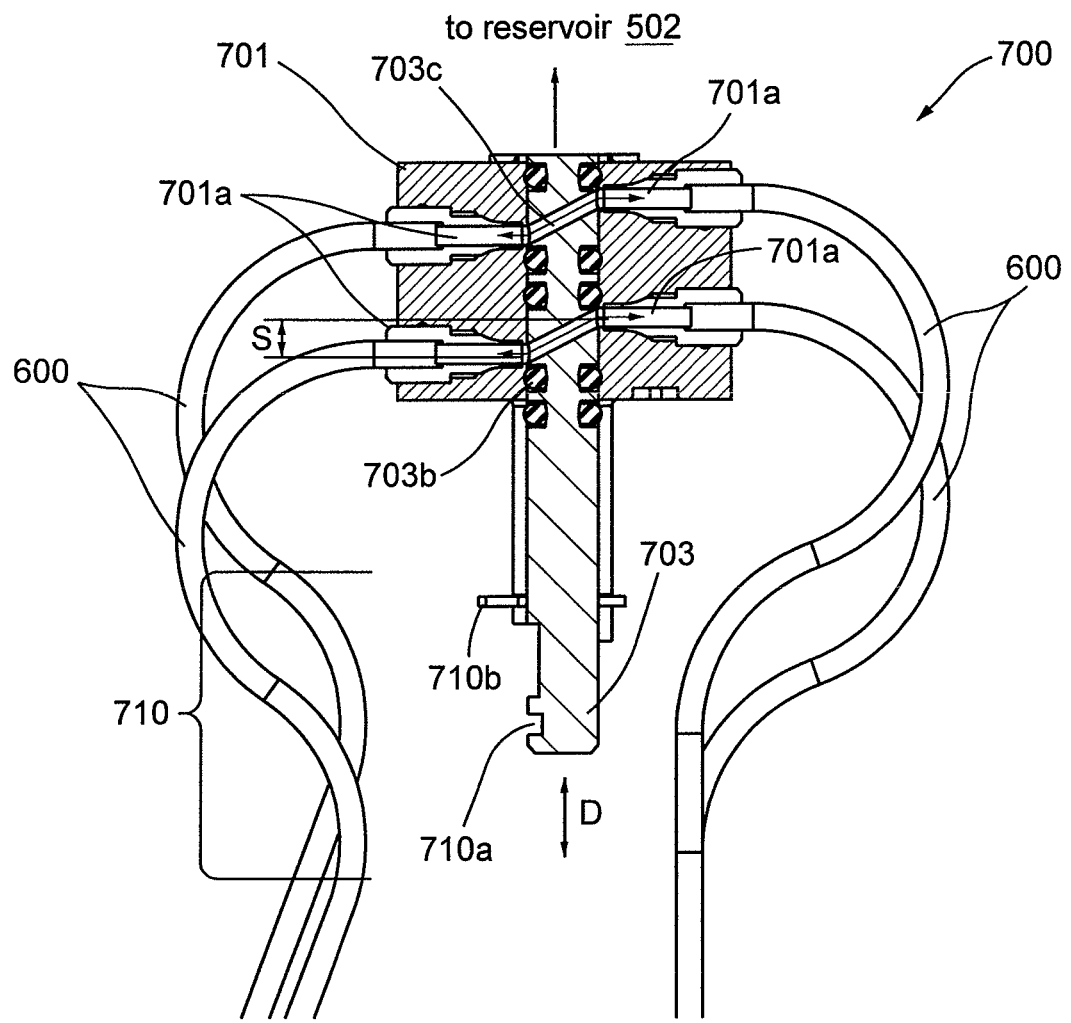
FIG. 9 is a close-up, partial cross-sectional side view of the exemplary spool valve 700 of FIG. 8 in a use mode.

FIG. 9 shows a close-up view of the exemplary spool valve 700 of FIG. 8 in use mode, in accordance with aspects of the present invention. The exemplary spool valve 700 also contains a spool 703 that may, among other things, control fluid communication among the ports on either side of the exemplary spool valve 700. The spool 703 may contain various features for obtaining fluid-tight seals to prevent cross communication, or other communication, of fluids within the spool 703 or among components in fluid communication with the spool 703. For example, FIG. 8 shows a spool valve with a series of O-rings 703b described above with respect to FIG. 8. The O-rings 703b may include any suitable material for providing a fluid-tight seal. For example, O-rings 703b may include a material such as, but not limited to, rubber, elastomer, polymer or plastic. The O-rings 703b can be completely impermeable to fluid, semi-permeable or selectively permeable. In addition, the spool 703 may contain other features, such as passageways or filters, that allow fluid communication among different portions of the spool 703. Although not shown in FIG. 9, the spool 703 may also contain other features for sealing hydraulic connections, including seal tubes.

As shown in FIG. 9, the spool 703 may include passageways 703c that allow fluid communication between ports 701a on either side of the spool 703. The passageways 703c in the spool 703 may be angled with respect to the passageways 503c shown in FIG. 5A in order to accommodate the staggering S of the ports 701a. As shown in FIG. 9, each of the ports 701a may be in fluid communication with an end of one of the passageways 703c.

Although two such passageways 703c are shown in FIG. 9, it is to be understood that any suitable number of passageways are possible, depending on the particular application. The spool valve 703 may also include devices and features for sealing off or preventing fluid communication via the passageways 703c. These devices and features may include O-rings 703b, valves or stoppers, amongst other features. The devices and features may be composed of rubber, polymer, plastic or combinations of any suitable material. Generally, the devices and features are not permeable to the hydraulic fluid; however, they may be permeable to other media. They may be semi-permeable and/or porous.

As also shown in FIG. 9, the exemplary spool valve 700 may further including a locking mechanism 710 for locking the spool 703 in a particular position. The locking mechanism 710 may include, for example, an acceptor portion 710a on the spool 703 for accepting tab 710b, for example. The relative positions of the acceptor portion 710a and the tab 710b may be placed in other suitable locations, or even substantially reversed so that the spool 703 includes a tab 710b. In order to engage the locking mechanism 710, for example, the user may move the spool 703 along direction D, such that the tab 710b is aligned with the acceptor mechanism 710a and, subsequently, insert the tab 710b into the acceptor portion 710a. The position in which the tab 710b is aligned with the acceptor mechanism 710a may correspond to any one of the various modes (brake, use or storage) of the device, depending on the relative placement of the locking mechanism 710.

In fact, any of the variations discussed herein may include multiple locking mechanisms 710 to lock in any one of the various modes (e.g., brake, use or storage). In addition, the locking mechanism 710 may be placed in other positions, such that the spool 703 can be locked in place in a position that does not correspond directly to the various modes discussed herein. Optionally, the locking mechanism 710 may be biased to a locked or unlocked position (e.g., if biased to a locked position, moving the spool 703 to the locking position will result in automatic locking in that position).

In use mode, as shown in FIG. 9, hydraulic fluid communication among various portions of the device may be limited by the construction of the spool 703. More particularly, fluid communication may be limited by the spool 703 to the passageways 703c. In use mode, the spool 703 may prevent fluid communication among the reservoir 502 and the slave and control portion of the device. Hydraulically isolating the reservoir 502 from the hydraulically active portions of the device (e.g., the slave and control portions), may allow hydraulic pressure from the control cylinders in the control portion the device to actuate control cylinders in the slave portions of the device.

The exemplary spool valve 700 may be placed in use mode by moving the spool 703 axially along the direction D until it reaches the position shown in FIG. 9. However, it is to be understood that the spool valve 700 could be constructed, within the context hereof, such that use mode is accessed when the spool 703 is in another position. Further, the spool 703 and the passageways 703c could have any suitable alternative construction such that use mode is accessed by some other motion of the spool 703. For example, the passageways 703c in the spool could be constructed so that use mode is accessed by rotating the spool 703 around its axis. Alternatively, it is within the scope of the invention that the spool and the passageways 703c in the spool 703 could be constructed such that use mode is accessed by moving the spool 703 laterally, or in the direction parallel to the flow of hydraulic fluid through the passageways 703c. It is also within the scope of the invention that the passageways 703c may be constructed such that use mode is accessed when the spool 703 is put through a more complicated motion (e.g., one that involves some combination of vertical, lateral and/or rotational motion).

Figure 10:
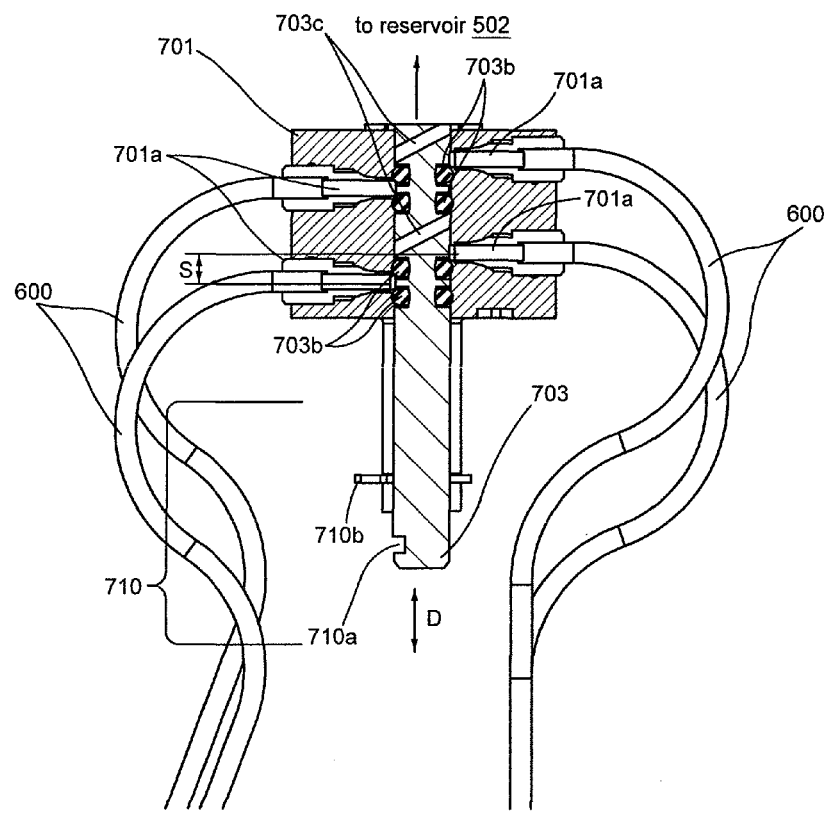
FIG. 10 is a close-up, partial cross-sectional side view of the exemplary spool valve 700 of FIG. 8 in a brake mode.

FIG. 10 shows a close-up view of the exemplary spool valve 700 in brake mode, in accordance with aspects of the present invention. As shown in FIG. 10, in brake mode, the spool 703 may be positioned so that the passageways 703c that allow fluid communication between fluid lines 600 on either side of the spool 703 in use mode are not in fluid communication with the hydraulic lines 600. As also shown in FIG. 10, the ends of the passageways 703c in brake mode may be hydraulically separated from the ports 701a via O-rings 703b. The O-rings 703b serve to isolate the passageways 703c from the ports 701a in brake mode, in some cases, even up to pressures beyond 3000 psi. Other devices and features for sealing off the hydraulic lines 600, not shown in FIG. 10, may also be included.

These other devices may include seal tubes and/or other components and generally may comprise a material such as rubber, elastomer, polymer or other elastic material. Similarly, the O-rings may comprise a material such as rubber, elastomer, polymer or other elastic material. However, the O-rings 703b and other devices and features may also include other suitable materials for creating a fluid-tight seal, including combinations of materials already mentioned, as well as other suitable materials. In some respects, the O-rings 703b and other devices and features are not permeable to the hydraulic fluid 120; however, they may be permeable to other media. In some aspects, seal tubes or O-rings 703b may be semi-permeable and/or porous. In certain cases, they may even be permeable to hydraulic fluids. Further, the O-rings 703b and other devices and features may include clips, clamps or other mechanical devices for securing the connections with the hydraulic lines 600. The O-rings 703b and other devices and features generally may serve as a barrier to fluid flow from the hydraulic lines 600.

One of the advantages of the brake mode of the spool valve 700, among others, may be to prevent user actuation of the control cylinders in the slave portions of the device when actuation of the slave portion control cylinders is not necessary and/or possibly detrimental. For example, during surgery it may be necessary to pause to allow the patient to reach a stable condition, for necessary tools and/or resources (e.g., medications) to be delivered, or for the surgeon to simply take a break. In addition, multiple surgeons may be present for performing different aspects of a single procedure. When a new surgeon takes over the operation, it may be necessary to lock the device in brake mode so that inadvertent contact with the control portion of the device in the changeover does not cause damage to the device, the patient or other aspects of the operating theater. In each of these situations, as well as others, it may be necessary to immobilize tools used by the device temporarily, so that no detriment occurs to the patient or any other aspect of the operation while the device is not in use. Brake mode may cut the hydraulic connection between the control and slave portions of the device to prevent transfer of an input to the control portion from being translated into an output at the slave portion, such as to prevent damage being caused by inadvertent actions on the control portion of the device.

In brake mode, as shown in FIG. 10, hydraulic fluid communication among various portions of the device may be prevented by the construction of the spool 703. More particularly, the slave and control portions of the device may be prevented from being in fluid communication when the exemplary spool valve 700 is in brake mode. In brake mode, O-rings 703b or the seal tubes of the spool 703 also may prevent fluid communication between the reservoir 502 and the slave and control portion of the device. In brake mode, being a variant of use mode, the reservoir 502 is kept isolated. The reservoir 502 remains isolated to prevent unwanted exchange of fluid between either cylinder and the reservoir, which could result fluid pressure loss or other adverse effects.

The exemplary spool valve 700 may be placed in brake mode by moving the spool 703 to the position shown in FIG. 10. However, it is to be understood that the spool valve 700 could be constructed, within the context hereof, such that brake mode is accessed when the spool 703 is in another position. Further, the spool 703, the passageways 703c, the ports 701a and the O-rings 703b could have any suitable alternative construction such that brake mode is accessed by some other motion of the spool 703. For example, the passageways 703c, the ports 701a and the O-rings 703b in the spool could be constructed so that brake mode is accessed by rotating the spool 703 about its axis. Alternatively, it is within the scope hereof that the spool, the passageways 703c, the ports 701a, and the O-rings 703b in the spool 703 could be constructed such that brake mode is accessed by moving the spool 703 laterally, or in the direction parallel to the flow of hydraulic fluid through the passageways 703c. It is also within the scope hereof that the passageways 703c be constructed such that brake mode is accessed when the spool 703 is put through a more complicated motion (e.g., one that involves some combination of vertical, lateral and/or rotational motion).

Figure 11:
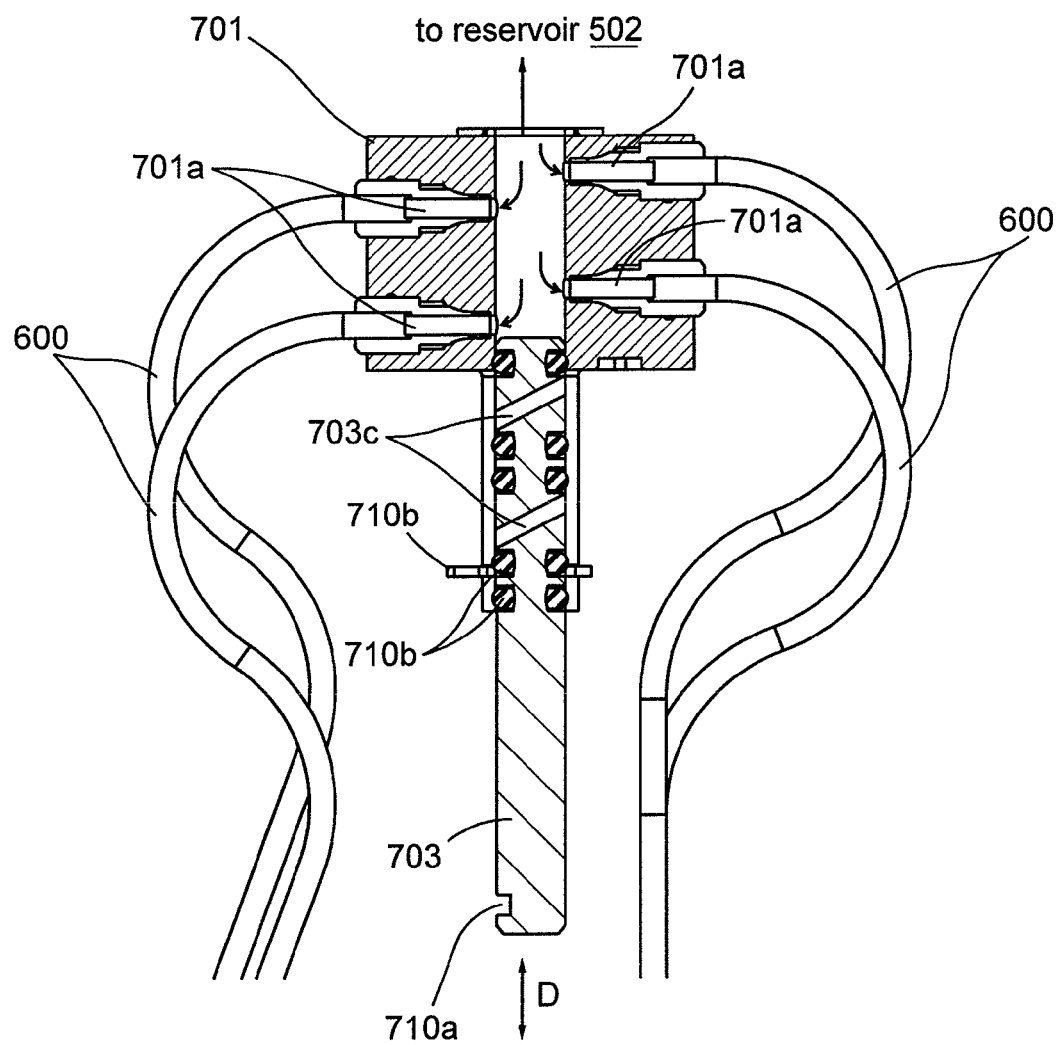
FIG. 11 is a close-up, partial cross-sectional side view of the exemplary spool valve 700 of FIG. 8 in a storage mode.

FIG. 11 shows a close-up view of the exemplary spool valve 700 in storage mode, in accordance with aspects of the present invention. As shown in FIG. 11, in storage mode, each of the hydraulic lines 600 may be in fluid communication with both the reservoir 502 and with each of the other hydraulic lines 600. Thus, the spool 703 may be in such a position so as to render each of the control cylinders in the slave and control portion of the device connected to the reservoir 502 in the same hydraulic circuit. This position may have the effect of de-coupling each of the control cylinders in the control portion of the device from its respective control cylinder in the slave portion of the device, much as in brake mode (FIG. 10). Unlike in brake mode, however, this de-coupling may be accomplished by placing all of the control cylinders of the device in fluid communication with each other and with the reservoir 502, thereby creating equilibrium.

One of the purposes of storage mode, among others, may be to keep the hydraulic circuits hydrated. The list of these situations discussed with reference to brake mode above may apply equally to storage mode. Storage mode also may cut the hydraulic connection between the control and slave portions of the device to prevent such damage being caused by inadvertent actions of the control portion of the device. Unlike in brake mode, however, each hydraulic device in the system may be connected to the reservoir 502 in storage mode. In an aspect, for example, one of the purposes of connecting each of the control cylinders 100 and hydraulic lines 600 to the reservoir 502 may be to allow the reservoir 502 to replenish hydraulic fluid in the system that may be lost, for example, due to evaporation or leakage. Replenishing the fluid can be especially useful if the hydraulic tubes 600 are semi-permeable to the hydraulic fluid and allow evaporation. In storage mode, the device may lie dormant for long periods of time, making evaporation of the hydraulic fluid a much more pressing issue than in any other mode. Since use mode and brake mode are generally employed for relatively brief periods, the amount of evaporation and/or fluid loss due to leakage may be slight.

In storage mode, as shown in FIG. 11, hydraulic fluid communication among various portions of the device may be equalized via the placement of the spool 703 relative to the ports 701a such that all ports 701a connect to each other and to reservoir 502. More particularly, each control cylinder of the slave and control portion of the device may be in fluid communication with each of the other control cylinders of the device when the exemplary spool valve 700 is in storage mode. This fluid communication means that any inadvertent movement in a control cylinder in the control portion of the device causes an increase in hydraulic pressure that is not directly transferred to the corresponding control cylinder in the slave portion of the device, as the movement causes hydraulic pressure to be distributed throughout the system and to the reservoir 502. In storage mode, generally the O-rings 703b of the spool 703 are not used to prevent fluid communication between the reservoir 502 and the slave and control portion of the device. Rather, the position of the spool 703 may prevent these components from contacting the hydraulic fluid. Thus, placing each of the control cylinders of the device in fluid communication with each other and the reservoir 502 can prevent hydraulic pressure from the control cylinders in the control portion the device from actuating control cylinders in the slave portions of the device.

The exemplary spool valve 700 may be placed in storage mode by moving the spool 703 axially along the direction D to the position shown in FIG. 11. However, it is to be understood that the spool valve 700 could be constructed, within the context hereof, such that storage mode is accessed when the spool 703 is in another position. For example, the spool 703 could be constructed with a region that has additional passageways that serve to connect each of the ports 701*a* to the reservoir 502. Further, the spool 703 could have any suitable alternative construction such that storage mode is accessed by some other motion of the spool 703. For example, the spool could be constructed so that storage mode is accessed by rotating the spool 703 around its axis. Alternatively, it is within the scope hereof that the spool 703 could be constructed such that storage mode is accessed by moving the spool 703 laterally, or in the direction parallel to the flow of hydraulic fluid through the passageways 703*c*. It is also within the scope of the invention that the spool 703 is constructed such that brake mode is accessed when the spool 703 is put through a more complicated motion (e.g., one that involves some combination of vertical, lateral and/or rotational motion).

Although aspects of the invention have been described with reference to variations and examples with respect to a surgical instrument, it is within the scope and spirit hereof to incorporate or use such variations and examples with any suitable mechanical device. Further, while some features have been described with reference to a surgeon, aspects of the invention may be used with another user, depending on circumstances of use. Thus, it should be understood that numerous and various modifications may be made without departing from the spirit hereof.

The invention claimed is:

1. A spool valve comprising:
a body portion having at least two ports and a spool-receiving opening; and
a spool slideably retained within the opening of the body portion, the spool having at least one passageway moveable to a first position so as to communicate with the at least two ports,
wherein the spool is positionable in a second spool position wherein the at least two ports are not in communication; and
wherein the spool is positionable in a third spool position wherein the at least two ports are in communication with a reservoir that stores hydraulic fluid.

2. The spool valve of claim 1, wherein in the first spool position the at least two ports are not in communication with the reservoir that stores hydraulic fluid.

3. The spool valve of claim 1, wherein in the second spool position the at least two ports are not in communication with the reservoir that stores hydraulic fluid.

4. The spool valve of claim 1, wherein in the third spool position the at least one passageway is not in communication with the at least two ports.

5. The spool valve of claim 1, the spool valve further comprises:
a sealing member, wherein in the second spool position, the at least one sealing member is aligned with at least one of the at least two ports.

6. The spool valve of claim 1, wherein the at least one passageway is angled with respect to a longitudinal axis of the spool.

7. The spool valve of claim 1, wherein the body portion further comprises:
a locking mechanism engageable with an acceptor portion of the spool.

8. The spool valve of claim 7, wherein engagement of the locking mechanism with the acceptor portion corresponds to one of the first, second, and third spool positions.

9. The spool valve of claim 8, wherein the locking mechanism includes a tab member.

10. A hydraulically driven surgical device comprising:
a control portion, the control portion having at least one control cylinder and an actuation portion;
a slave portion hydraulically connected to the control portion, the slave portion having at least one slave cylinder fluidly actuable by the at least one control cylinder; and
a spool valve operatively located between the control portion and the slave portion, the spool valve having:
a body portion having at least two ports and a spool-receiving opening; and
a spool slideably retained within the opening of the body portion, the spool having at least one passageway moveable to a first position so as to communicate with the at least two ports,
wherein the spool is positionable in a second spool position wherein the at least two ports are not in communication; and
wherein the spool is positionable in a third spool position wherein the at least two ports are in communication with a reservoir that stores hydraulic fluid.

11. The hydraulically driven surgical device of claim 10, wherein in the first spool position the at least two ports are not in communication with the reservoir that stores hydraulic fluid.

12. The hydraulically driven surgical device of claim 10, wherein in the second spool position the at least two ports are not in communication with the reservoir that stores hydraulic fluid.

13. The hydraulically driven surgical device of claim 10, wherein in the third spool position the at least one passageway is not in communication with the at least two ports.

14. The hydraulically driven surgical device of claim 10, wherein the spool valve further comprises:
at least one sealing member, wherein in the second spool position, the at least one sealing member is aligned with at least one of the at least two ports.

15. The hydraulically driven surgical device of claim 10, wherein the at least one passageway is angled with respect to a longitudinal axis of the spool.

16. The hydraulically driven surgical device of claim 10, wherein the body portion further comprises:
a locking mechanism engageable with an acceptor portion of the spool.

17. The hydraulically driven surgical device of claim 16, wherein engagement of the locking mechanism with an acceptor portion corresponds to one of the first, second, and third spool positions.

18. The hydraulically driven surgical device of claim 17, wherein the locking mechanism includes a tab member.

19. A method of operating a hydraulically driven surgical device comprising:
actuating a control portion of the hydraulically driven surgical device;
providing a spool valve operatively connected to the control portion and a slave portion of the hydraulically driven surgical device, the spool valve including:
a body portion having at least two ports and a spool-receiving opening; and
a spool slideably retained within the opening of the body portion, the spool having at least one passageway moveable to a first position so as to communicate with the at least two ports, a second spool position wherein the at least two ports are prevented from communication, and a third spool position, and wherein the at least two ports are in communication with a reservoir that stores hydraulic fluid.

20. The method of claim 19, further comprising:
positioning the spool in the second spool position wherein the at least two ports are prevented from communication.

21. The method of claim 19, wherein in the first position the at least two ports are not in communication with the reservoir that stores hydraulic fluid.

22. The method of claim 19, wherein in the second position the at least two ports are not in communication with the reservoir that stores hydraulic fluid.

23. The method of claim 19, further comprising:
positioning the spool in the third position wherein the at least two ports are in communication with the reservoir.

24. The method of claim 23, wherein in the third position the at least one passageway is not in communication with the at least two ports.

25. The method of claim 23, wherein the body portion further comprises a locking mechanism engageable with an acceptor portion of the spool.

26. The method of claim 25, wherein the locking mechanism includes a tab member.

27. The method of claim 19, wherein the spool valve further comprises:
at least one sealing member, wherein in the second position, the at least one sealing member is aligned with at least one of the at least two ports.

28. The method of claim 19, wherein the at least one passageway is angled with respect to a longitudinal axis of the spool.

29. The method of claim 28, further comprising:
engaging the locking mechanism with the acceptor portion thereby retaining the spool in one of the first, second, and third spool positions.

* * * * *